United States Patent [19] [11] 4,196,136
Knoth, Jr. [45] Apr. 1, 1980

[54] LIGATED TRANSITION METAL DERIVATIVES OF HETEROPOLYANIONS

[75] Inventor: Walter H. Knoth, Jr., Mendenhall, Pa.

[73] Assignee: E. I. Du Pont de Nemours and Company, Wilmington, Del.

[21] Appl. No.: 957,691

[22] Filed: Nov. 6, 1978

[51] Int. Cl.$^2$ .............................................. C07F 7/22
[52] U.S. Cl. ........................... 260/429.7; 260/429 R; 260/429 CY; 260/429 L; 260/439 CY; 423/306; 423/307; 423/326; 423/593; 423/594
[58] Field of Search ..... 260/429 CY, 429 R, 439 CY, 260/429 L, 429.7; 423/306, 326, 307, 593, 594

[56] References Cited

U.S. PATENT DOCUMENTS

| 2,554,597 | 5/1951 | Starnes et al. ............... 423/326 X |
| 3,069,449 | 12/1962 | Gorsich .................. 260/429 CY X |
| 3,243,258 | 3/1966 | Smit et al. .......................... 423/306 |
| 3,320,293 | 5/1967 | Coffey .................... 260/429 CY X |
| 3,361,518 | 1/1968 | Chiola et al. ................... 423/594 X |
| 3,425,794 | 2/1969 | Chiola et al. ................... 423/326 X |
| 3,428,415 | 2/1969 | Chiola et al. ......................... 423/593 |
| 3,446,575 | 5/1969 | Chiola et al. ................... 423/326 X |
| 3,752,776 | 8/1973 | Chester et al. ................. 423/593 X |
| 3,804,870 | 4/1974 | Hughes et al. ............. 260/429 CY X |
| 3,947,332 | 3/1976 | Vanderpool et al. ............ 423/307 X |
| 4,012,399 | 3/1977 | Hechenbleikner et al. ... 260/429 CY X |
| 4,115,425 | 9/1978 | Karol et al. ................ 260/429 CY X |
| 4,124,647 | 11/1978 | McVicker .................. 260/429 CY X |

OTHER PUBLICATIONS

Mellor, A Comprehensive Treatise on Inorg. and Theo-Chem., Longmans, Green & Co., N.Y., V6 pp. 866-882 (1925).
Bailar, The Chemistry of the Coordination Compounds, Reinhold Publ. Co., N.Y., pp. 472-486 (1956).

*Primary Examiner*—Helen M. S. Sneed

[57] ABSTRACT

Salts and acids containing a triheteropolyanion in which one addenda atom of a heterododecatungstate or heterododecamolybdate is replaced by one tin atom or by two germanium atoms, in which the tin atom or the germanium atoms are bonded to a ligated transition metal, have outstanding utility as catalysts for the oligomerization of terephthalic acid with ethylene glycol, and for the isomerization of 1-butene, and for the dehydration of 2-butanol and subsequent isomerization of the 1-butene formed.

7 Claims, No Drawings

LIGATED TRANSITION METAL DERIVATIVES OF HETEROPOLYANIONS

TECHNICAL FIELD

This invention relates to compounds containing transition metal derivatives of heteropolyanions.

BACKGROUND ART

Heteropolyanions are familiar chemical entities, and a great variety of acids and salts containing them are known. They are reviewed, for example, by Baker in "Advances in the Chemistry of the Coordination Compounds", Kirschner, Ed., p 604 (MacMillan, 1961); by Evans in "Perspectives in Structural Chemistry", Vol. IV, Dunitz and Ibers, Ed., p 1 (Wiley, 1971); by Weakley in "Structure and Bonding", Vol. 18, p 131 (Springer-Verlag, 1974); and by Sasaki and Matsumoto in J. Japan, Chem., 29, 853 (1975).

Typical heteropolyanions are dodecatungstosilicate or 12-tungstosilicate, $SiW_{12}O_{40}^{4-}$, and dodecamolybdophosphate or 12-molybdophosphate, $PMo_{12}O_{40}^{3-}$. In these anions the silicon and phosphorus atoms are usually designated as "central" atoms and the tungsten and molybdenum atoms are referred to as "addenda" atoms (Baker) or "peripheral" atoms (Chemical Abstracts). Molybdenum, tungsten, and vanadium are the most common addenda atoms. About 45 other elements, including most transition metals, can function as central atoms. Tungstosilicates and molybdophosphates are frequently referred to also as silicotungstates and phosphomolybdates and are sometimes formulated as, for example, $W_{12}SiO_{40}^{4-}$ and $Mo_{12}PO_{40}^{3-}$.

Heteropolyanions are most stable in solutions of relatively low pH. It is known that by raising the pH, an addenda atom and one accompanying oxygen atom can be removed selectively from certain heteropolyanions (e.g., a $WO^{4+}$ moiety from $SiW_{12}O_{40}^{4-}$). By a number of methods, the cavity then present in the heteropolyanion cage can be filled by a different atom, such as chromium, manganese, iron, cobalt, nickel, copper, or gallium. See, for example, Baker et al., J. Am. Chem. Soc., 88, 2329 (1966); Weakley and Malik, J. Inorg. Nucl. Chem., 29 2935 (1967); and Tourné et al., Bull. Soc. Chem., 1969, 1124, and J. Inorg. Nucl. Chem., 32, 3875 (1970).

The anions resulting from these "substitutions" are frequently designated in abbreviated fashion as, for example, $XZW_{11}$, where X is the original, central or "inner" hetero atom and Z is the new, "outer" hetero atom. X has also been used to designate a pair of atoms, i.e., hydrogen atoms. These "substituted" heteropolyanions have been referred to as triheteropolyanions, in accordance with the presence of three different kinds of positive-valent atoms. Baker and Figgis, J. Am. Chem. Soc., 92, 3794 (1970) and Weakley, J. Chem. Soc. Dalton, 1973, 341, have shown that an outer hetero atom in such a heteropolyanion can be bonded to a ligand such as water, pyridine, or halide ion. These conclusions have been disputed by Komura et al, Bull. Chem. Soc. Japan, 49 (1), 87 (1976).

In the field of transition metal chemistry, a large number of compounds are known in which ligated transition metals are bonded directly to ligated Group IVb elements other than carbon, e.g., silicon, germanium, and tin. A review article published in 1970 reports that the number of such compounds had risen from a few dozen in the early 1960's to more than 500; see Brooks and Cross, Organometal. Chem. Rev. A, 1970, 227. Many more such compounds have been reported since 1970.

Regarding the ligands bonded to transition metals in such compounds, Brooks and Cross point out that in general the same ligand configurations that give stable organo transition metal complexes also give stable group IVb metal derivatives. For example, the configuration $\pi\text{-}C_5H_5(CO)_2Fe-$ is a common one; stable compounds are known in which it is bonded to itself, to halogen, to hydrocarbyl, and to metals such as sodium and mercury. Correspondingly, Brooks and Cross list a number of stable compounds in which the $\pi\text{-}C_5H_5(CO)_2Fe-$ grouping is bonded to silicon, germanium, or tin, the Group IVb atom being bonded in turn to ligands such as halo or hydrocarbyl. In addition to $\pi$-cyclopentadienyl and carbonyl, other ligands that are bonded to transition metal compounds in the many examples listed by Brooks and Cross include $\pi$-benzene, phenanthroline, bipyridine, phenyl, trihydrocarbylphosphine, trihydrocarbyl phosphite, trihydrocarbylstibine, dihydrocarbyl sulfide, trihydrocarbylarsine, cyano, cyclooctadiene and norbornadiene.

DISCLOSURE OF INVENTION

The products of the present invention are salts and acids each containing a triheteropolyanion in which one addenda atom of a heterododecatungstate or heterododecamolybdate is replaced by one tin atom or by two germanium atoms, each of which tin or germanium atoms is bonded to a ligated transition metal atom.

The products of the invention have the following distinguishing characteristics:

1. The original hetero atom, i.e., the central atom, of the heterododecaanion does not become bonded directly to a new entering group, in particular to a ligated transition metal-tin or -germanium moiety.
2. The added ligated transition metal is not part of the dodecanuclear cage structure.
3. The heteropolyanion contains at least one metal-metal bond, which is outside the skeletal structure of the heteropolyanion.

The products of the invention can be grouped by formulas into several different types.

Products of type 1 have the formula

$$[Q^+]_a[L_bMSnM'_{11}XO_{39}]^{a-} \qquad (1)$$

Formula (1) is written to bring out the ionic nature of the product. It can also be written simply as $Q_aL_bMSnM'_{11}XO_{39}$.

In formula (1)

$Q^+$ is one equivalent of a cation;

the moiety $L_bM$ comprises a ligated transition metal M bonded to b ligands L, b is at least 1, and the ligands can be the same or different when b is greater than 1;

M' is W or Mo;

X is Si, P, Co, or Ge; and a is the number of formal negative charges on the heteropolyanion $L_bMSnM'_{11}XO_{39}$, and is usually 4–8. When "a" is greater than 1, the Q's can be the same or different.

As will be apparent from the examples, the products of this invention are usually prepared in aqueous or partly aqueous media and are most readily isolated as hydrates corresponding to various degrees of hydration. These hydrates are included in the invention and, accordingly, the claims should be interpreted as including hydrates of the claimed products.

Suitable products of type 1 include
[(CH$_3$)$_4$N]$_5$(CO)$_4$CoSnW$_{11}$SiO$_{39}$,
[(CH$_3$)$_3$NH]$_5$π-C$_5$H$_5$Fe(CO)$_2$SnW$_{11}$SiO$_{39}$,
[(CH$_3$)$_3$NH]$_5$π-C$_5$H$_5$Ru(CO)$_2$SnW$_{11}$SiO$_{39}$,
[(CH$_3$)$_3$NH]$_5$(dimethylglyoxime)$_2$Co(NC$_5$H$_5$)CoSnW$_{11}$SiO$_{39}$,
K$_5$π-C$_5$H$_5$Fe(CO)$_2$SnW$_{11}$SiO$_{39}$,
[(CH$_3$)$_4$N]$_5$p-FC$_6$H$_4$Pt[P(C$_2$H$_5$)$_3$]$_2$SnW$_{11}$SiO$_{39}$,
[(CH$_3$)$_4$N]$_5$C$_6$H$_5$Pt[PC$_2$H$_5$)$_3$]$_2$SnW$_{11}$GeO$_{39}$,
[(CH$_3$)$_3$NH]$_4$π-C$_5$H$_5$Fe(CO)$_2$SnW$_{11}$PO$_{39}$,
[(CH$_3$)$_3$NH]$_5$π-C$_5$H$_5$Ni(CO)SnW$_{11}$GeO$_{39}$,
K$_4$π-C$_5$H$_5$Fe(CO)$_2$SnW$_{11}$PO$_{39}$,
[(CH$_3$)$_4$N]$_5$π-C$_5$H$_5$W(CO)$_3$SnW$_{11}$SiO$_{39}$,
[(CH$_3$)$_4$N]$_5$π-C$_5$H$_5$Mo(CO)$_2$P(C$_6$H$_5$)$_3$SnW$_{11}$SiO$_{39}$,
K$_8$(CO)$_3$Co(SnO$_3$)SnW$_{11}$PO$_{39}$,
[(CH$_3$)$_4$N]$_7$π-C$_5$H$_5$Fe(CO)$_2$SnW$_{11}$CoO$_{39}$,
[(CH$_3$)$_4$N]$_7$(n-C$_4$H$_9$)$_3$PCo(CO)$_3$SnW$_{11}$CoO$_{39}$,
[(CH$_3$)$_4$N]$_5$(CO)$_2$Fe(NO)[P(C$_6$H$_5$)$_3$]SnW$_{11}$SiO$_{39}$,
[(CH$_3$)$_4$N]$_5$(C$_6$H$_5$O)$_3$PFe(CO)$_2$(NO)SnW$_{11}$GeO$_{39}$,
[(CH$_3$)$_3$S]$_4$[H]π-C$_5$H$_5$Fe(CO)$_2$SnMo$_{11}$SiO$_{39}$,
[(CH$_3$)$_3$S]$_4$[H]π-C$_5$H$_5$Mo(CO)$_2$P(OCH$_3$)$_3$SnMo$_{11}$SiO$_{39}$,
[(CH$_3$)$_3$S]$_4$[H]π-C$_5$H$_5$Ru(CO)$_2$SnMo$_{11}$SiO$_{39}$,
[(CH$_3$)$_3$S]$_4$[H][(C$_6$H$_5$)$_2$PCH$_2$CH$_2$P(C$_6$H$_5$)$_2$]$_2$Re(CO)SnMo$_{11}$SiO$_{39}$,
[(CH$_3$)$_4$N]$_{10}$SnW$_{11}$SiO$_{39}$Co(CO)$_3$SnMo$_{11}$SiO$_{39}$,
[(CH$_3$)$_3$NH]$_4$(C$_7$H$_8$)$_2$RhSnW$_{11}$PO$_{39}$,
[(CH$_3$)$_3$NH]$_5$(CH$_7$H$_8$)$_2$IrSnW$_{11}$SiO$_{39}$,
[(CH$_3$)$_3$NH]$_5$[(C$_6$H$_5$)$_3$As]$_2$C$_8$H$_{12}$IrSnW$_{11}$GeO$_{39}$,
[(CH$_3$)$_3$NH]$_5$C$_7$H$_8$Co(CO)$_2$SnW$_{11}$SiO$_{39}$,
[(CH$_3$)$_3$NH]$_5$π-C$_5$H$_5$Fe(CO)$_2$SnW$_{11}$GeO$_{39}$,
[(CH$_3$)$_3$NH]$_4$[(C$_6$H$_5$)$_3$P]$_2$C$_7$H$_8$RhSnW$_{11}$PO$_{39}$,
[(CH$_3$)$_3$NH]$_5$(C$_6$H$_5$)$_3$P(π-C$_3$H$_5$)PdSnW$_{11}$SiO$_{39}$,
K$_5$[(C$_6$H$_5$)$_3$P]$_2$Ir(CO)(H)$_2$SnW$_{11}$SiO$_{39}$,
Ba$_5$[π-C$_5$H$_5$Mo(CO)$_2$P(OCH$_3$)$_3$SnW$_{11}$GeO$_{39}$]$_2$,
[(C$_2$H$_5$)$_4$As]$_4$π-C$_5$H$_5$Ru(CO)$_2$SnW$_{11}$PO$_{39}$,
Li$_5$π-C$_5$H$_5$Ni(CO)SnW$_{11}$SiO$_{39}$,
Zn$_7$[(C$_7$H$_8$)Co(CO)$_2$SnW$_{11}$CoO$_{39}$]$_2$,
Cs$_5$(C$_6$H$_5$O)$_3$P(NO)(CO)$_2$FeSnMo$_{11}$GeO$_{39}$,
K$_4$[(C$_6$H$_5$)$_3$As](CO)$_3$CoSnW$_{11}$PO$_{39}$,
H$_5$[(C$_6$H$_5$)$_3$P](CO)$_3$CoSnW$_{11}$GeO$_{39}$,
and their hydrates.

The sole function of Q in compounds of formula (1) is to provide a counter-ion or -ions for the novel heteropolyanion, which is the essence of the invention. To put it another way, the sole purpose of Q is to provide a means for isolating the novel heteropolyanion in compound form. The properties of Q, therefore, are not critical and Q can represent a broad range of elements or combination of elements. Only one limitation on the very broad nature of Q is known. Since the products of the invention are made and frequently used in the presence of water, the cation Q should be reasonably stable to water.

Because of availability and ease of preparation of new products containing them, preferred values of Q are hydrogen, alkali metal, one equivalent of alkaline-earth metal, NH$_4$, RNH$_3$, RR'NH$_2$, RR'$_2$NH, RR'$_3$N, R$_4$P, R$_3$S, R$_4$As, or R$_4$Sb, wherein R' is aliphatically saturated hydrocarbyl bonded to N through aliphatic carbon and contains up to 18 carbons and preferably up to 12 carbons, and R is aliphatically saturated hydrocarbyl of up to 18 carbons and preferably up to 12 carbons. Any two R and R' groups in the same cation can also be joined (bonded) to each other directly or through an ethereal oxygen atom to form a divalent, aliphatically saturated hydrocarbyl or oxygen-interrupted (monooxa) hydrocarbyl group of up to 18 carbons and preferably up to 12 carbons. Most preferably this divalent group is alkylene of 4–8 carbons. "Aliphatically saturated hydrocarbyl" is defined as hydrocarbyl that does not contain any ethylenic or acetylenic carbon-carbon unsaturation, i.e., the hydrocarbyl groups can be alkyl, cycloalkyl, aryl, alkaryl, or aralkyl. Thus the term refers to hydrocarbyl in which any unsaturation is aromatic.

Examples of the Q cations as defined above include hydrogen, sodium, potassium, rubidium, barium, calcium, strontium, magnesium, cesium, ammonium, methylammonium, cyclopropylammonium, 1-methylheptylammonium, 2-(1-naphthyl)ethylammonium, octadecylammonium, p-ethylanilinium, diisobutylammonium, dicyclohexylammonium, dinonylammonium, morpholinium, dodecamethyleniminium, triisopropylammonium, N-methylpiperidinium, trihexylammonium, dodecyldimethylammonium, tetraisopentylammonium, heptyltrimethylammonium, trimethylpentylammonium, cyclodecyltrimethylammonium, N,N-didodecylmorpholinium, dimethylanilinium, tetramethylphosphonium, tetranaphthylphosphonium, ethylpentamethylene-p-tolylphosphonium, dimethyloctadecylsulfonium, methyltetramethylenesulfonium, triethylsulfonium, tetraphenylarsonium, benzylhexadecyldimethylarsonium, dodecyltriethylarsonium, tetramethylstibonium, dibenzyldimethylstibonium, and the like.

Of the above R- and R'-substituted cations, those containing only lower alkyl (1-6 carbons) are preferred, especially tetramethylammonium and trimethylammonium. The latter are useful precipitating cations to give products containing the novel heteropolyanions in readily isolable form. Preferred cations overall are hydrogen, the alkali metals, and the ones in the first sentence of this paragraph.

Compounds of the invention in which Q is hydrogen are ordinarily isolated as solvates. Since these compounds are most commonly worked with in aqueous media, the most common types of solvates are hydrates. The exact position of attachment of the solvate molecules is not known, but at least some of them are almost certainly associated with the hydrogen ions. It is to be understood, therefore, that the term "hydrogen" as used here, includes, and in fact for all practical purposes always refers to, hydrogen ions solvated with water or other solvent molecules. When Q is hydrogen, the degree of solvation of the hydrogen ion is of no particular importance to the present invention. The above usage of the term "hydrogen" is based on nomenclature approved by the International Union of Pure and Applied Chemistry; see J. Am. Chem. Soc., 82, 5529–30 (1960).

As noted above, the ligand configurations in the ligated transition metal moiety L$_b$M, i.e., the nature of L and the value of b, will generally be the same as those that give stable complexes of the particular transition metal generally. Most specifically and for example, Brooks and Cross point out that in transition metal-Group IVb metal compounds the coordination sphere of chromium, molybdenum, or tungsten always includes a combination of π-bonding ligands. Common examples are combinations of π-benzene, π-cyclopentadienyl, or bipyridine with carbonyl. For manganese and rhenium the ligands are almost without exception carbonyls. With iron, ruthenium, and osmium the ligands are most frequently carbonyls or combinations of carbonyl with π-cyclopentadienyl. With metals of the cobalt group, compounds containing cobalt itself tend to contain carbonyl and cyclopentadienyl carbonyl ligands with properties comparable to those of manganese and iron; ligands attached to rhodium and iridium compounds tend more to be tertiary phosphines, arsines, and stibines, halide, hydride, and cyclopolyene ligands. Nickel compounds usually involve carbonyl or $\pi$-cyclopentadienyl ligands, whereas palladium and platinum derivatives tend more to phosphine, cyano, and cyclopolyene ligands. Overall the ligated transition metal moieties that will be operable will be quite familiar to one skilled in the art, particularly after a review of the Brooks and Cross article and of later publications on this subject. The foregoing illustrations are not intended to be limiting; in general any ligand, L, that can be present in a ligated transition metal-tin trihalide or -germanium trihalide can be present in a product of the invention.

From the foregoing discussion it will be seen that L can be a neutral ligand such as $\pi$-benzene, carbonyl, bipyridine, and phosphine or a ligand with a formal valence of $-1$ such as $\pi$-cyclopentadienyl, halide and hydride. A bidentate ligand such as bipyridine will be the equivalent of two L's.

The number of formal negative charges, a, on the novel heteropolyanion is of course the algebraic sum of the oxidation states of all the atoms in the anion. For example, in the heteropolyanion, $[(CO)_4CoSnW_{11}SiO_{39}]^{5-}$, of the product of Example 1 each oxygen is in an oxidation state of $-2$, each tungsten $+6$, and the silicon $+4$. The tin is assumed to be formally $+4$ (Brooks and Cross, page 38), and the cobalt is assigned $-1$, corresponding to its oxidation state in $HCo(CO)_4$. The four carbonyl groups are assumed to be neutral and not contribute formally to the charge on the heteropolyanion. The algebraic sum of the oxidation states of the one cobalt, one tin, one silicon, eleven tungstens and thirty-nine oxygens is $-5$, corresponding to the five tetramethylammonium cations present in the product.

One skilled in the art will be aware that because of the sometimes complex interactions between the various atoms of large anions of this type, the presence of metal-metal bonds, the variable oxidation states of transition metals, and the known uncertainties regarding oxidation states in some transition metal complexes, assignment of oxidation states in some instances will have to be rather arbitrary. Although the overall formal charge on the heteropolyanion in products of the invention can usually be accurately predicted and calculated, the best method of determining this charge is probably the empirical one of finding out the number of cation equivalents present via analysis.

Products of type 1 in which X is Si, Ge or P are made by reacting a ligated transition metal-tin trichloride, $L_bM-SnCl_3$, with a salt or acid containing the heteropolyanion of composition $M'_{11}XO_{39}$. As noted previously, the latter reactant is made by raising the pH of a solution of a compound containing the corresponding $M'_{12}XO_{40}$ anion, by which process an M'O entity is removed. The $M'_{11}XO_{39}$-containing reactant can be prepared and isolated in advance; see preparation of $K_8W_{11}SiO_{39}$ below and its use in several examples. Alternatively the $M'_{11}XO_{39}$-containing reactant can be prepared and used in place without isolation. Tribromides or triiodides can be used in place of the trichlorides $L_bM-SnCl_3$.

Compounds of type 1 in which X is Co are prepared by a corresponding reaction with a salt or acid containing the heteropolyanion of composition $Co_2M'_{11}O_{39}\cdot H_2O$. In these heteropolyanions one cobalt is the central, inner hetero atom and the other is the twelfth atom of the heterododecaanion cage.

A rather specialized method for making a small group of compounds of type 1 is discussed below in connection with products of type 2.

Products of type 1 are usually isolated from aqueous reaction mixtures by addition of a "precipitating" cation, i.e., a cation that forms a relatively insoluble salt with the novel heteropolyanion in solution. Examples of such cations are tetramethylammonium, trimethylammonium, and trimethylsulfonium. Products of the invention containing cations other than these precipitating cations can be made from the primary products by conventional cation-exchange methods.

In most of the reactions involved in the preparation of type 1 products of the invention and products of other types discussed below, the ligated transition metal moiety $L_bM$ persists unchanged, and the reaction is essentially a straightforward insertion/metathesis. For a few $L_bM$ moieties, however, under certain conditions which cannot readily be predicted in advance, one ligand, L, is partly or entirely lost by the transition metal, and its place is taken by a triheteropolyanion moiety, $SnM'_{11}XO_{39}$. The products of the invention thus formed, designated type 2, have as an overall anionic component a structure in which two heteropolyanion moieties, each with tin as a new addenda atom, are bonded through the tins to a ligated transition metal atom. These products can be represented by the formula $$[Q^+]_a[L_{b-1}M(SnM'_{11}XO_{39})_2]^{a-}, \qquad (2)$$

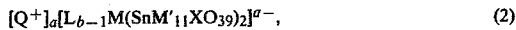

which also can be written simply as $Q_aL_{b-1}M(SnM'_{11}XO_{39})_2$. The terms in these formulas are defined as for formula (1), except that b is at least 2 and a is usually 9–11; the considerations noted for formula (1) also apply.

Each $SnM'_{11}XO_{39}$ moiety of a product of type 2, and therefore the overall anionic portion of such a product, has the three characteristics of a product of the invention listed above.

Suitable products of type 2 include
$[(CH_3)_3NH]_{11}(CO)_3Co(SnW_{11}SiO_{39})_2$,
$H_{11}(CO)_3Co(SnW_{11}SiO_{39})_2$,
$K_{11}(CO)_3Co(SnW_{11}SiO_{39})_2$,
$Na_{11}(CO)_3Co(SnW_{11}SiO_{39})_2$,
$[(CH_3)_3NH]_9(CO)_3Co(SnW_{11}PO_{39})_2$,
$K_9(CO)_3Co(SnW_{11}PO_{39})_2$,
$[(CH_3)_3NH]_{11}(CO)_2Fe(NO)(SnW_{11}SiO_{39})_2$,
$K_{11}(CO)_2Fe(NO)(SnW_{11}SiO_{39})_2$,
$[(CH_3)_3NH]_{11}\pi-C_3H_5Pd(SnW_{11}SiO_{39})_2$,
$Na_{11}(CO)_3Co(SnW_{11}GeO_{39})_2$,
$K_9(CO)_2(NO)Fe(SnW_{11}GeO_{39})_2$,
and their hydrates.

As noted above, products of type 2 are prepared by reacting particular ligated transition metal-tin trichlorides, $L_bM-SnCl_3$, with a salt or acid containing the heteropolyanion of composition $M'_{11}XO_{39}$. Example 15 illustrates preparation of a product of type 1 by reacting a type 2 product with potassium cyanide. In this reaction one of the $SnW_{11}PO_{39}^{3-}$ moieties bonded to cobalt becomes replaced by the L-type ligand $SnO_3^{3-}$.

Products of the invention of type 3 can be represented by the formula $$[Q^+]_a[(L_bMGe)_2M'_{11}XO_{40}]^{a-}, \qquad (3)$$

which can also be written simply as $Q_a(L_b\text{-}MGe)_2M'_{11}XO_{40}$. The terms in these formulas are defined as for formula (1) and the considerations noted for formula (1) again apply. In addition, each product of type 3 has the three characteristics of a product of the invention listed above.

Suitable products of type 3 include
$[(CH_3)_3NH]_4[\pi\text{-}C_5H_5Fe(CO)_2Ge]_2W_{11}SiO_{40}$,
$[(CH_3)_3NH]_3[\pi\text{-}C_5H_5Fe(CO)_2Ge]_2W_{11}PO_{40}$,
$[(CH_3)_3NH]_3[(C_6H_5)_3PCo(CO)_3Ge]_2W_{11}PO_{40}$,
$[(CH_3)_3NH]_4[(C_6H_5)_3AsCo(CO)_3Ge]_2W_{11}SiO_{40}$,
$[(CH_3)_3NH]_4[\pi\text{-}C_5H_5(C_2H_5)_3PNiGe]_2W_{11}GeO_{40}$,
$[(CH_3)_3NH]_4[\pi\text{-}C_5H_5Fe(CO)_2Ge]_2Mo_{11}SiO_{40}$,
$Cs_4[\pi\text{-}C_5H_5(CO)NiGe]_2W_{11}SiO_{40}$,
$(NH_4)_4[\pi\text{-}C_5H_5(CO)_2FeGe]_2W_{11}GeO_{40}$,
$[(C_2H_5)_2NH_2]_3[(C_6H_5)_3P(CO)_3CoGe]_2W_{11}PO_{40}$,
and their hydrates.

Products of type 3 are made by reacting a ligated transition metal-germanium trichloride, $L_bM\text{-}GeCl_3$, with a salt or acid containing the heteropolyanion composition $M'_{11}XO_{39}$. Tribromides or triiodides can be used in place of the trichlorides.

Products of type 4 can be represented by the formula $$[Q^+]_a[L_bM(GeOH)_2M'_{11}XO_{39}]^{a-}, \quad (4)$$

which also can be written simply as $Q_aL_bM(GeOH)_2M'_{11}XO_{39}$. The terms in these formulas are defined as for formula (1), and the considerations noted for formula (1) again apply. Suitable products of type 4 include
$[(CH_3)_3NH]_4\pi\text{-}C_5H_5Co(CO)(GeOH)_2W_{11}SiO_{39}$,
$[(CH_3)_3NH]_4\pi\text{-}C_5H_5Co(CO)(GeOH)_2W_{11}GeO_{39}$,
$[(CH_3)_3NH]_3(C_6H_5NC)_2Pd(GeOH)_2W_{11}PO_{39}$,
$K_3(C_6H_5NC)_2Pd(GeOH)_2Mo_{11}PO_{39}$,
and their hydrates.

Products of the invention of type 5 can be represented by the formula $$[Q^+]_a[L_bM(SnM'_{11}XO_{39})(SnM''_{11}X'O_{39})]^{a-}. \quad (5)$$

which can also be written simply as $Q_aSnM'_{11}XO_{39}L_bMSnM''_{11}X'O_{39}$. The terms in these formulas are defined as for formula (1), and the considerations noted for formula (1) again apply. M" is defined the same as M', and X' is defined the same as X; at least one of M" and X' is different from M' and X, respectively. M is preferably Co. It will be apparent that these products are quite similar to type 2, the difference being that the two heteropolyanion structures bonded through tin to a ligated transition metal are different instead of the same. Suitable products of type 5 include $[(CH_3)_4N]_{10}(SnW_{11}SiO_{39})Co(CO)_3(SnW_{11}PO_{39})$.

When the ligated transition metal-containing starting material used to prepare a product of the invention is a germanium trichloride (or tribromide or triiodide), $L_bM\text{-}GeCl_3$, in which the $L_bM$ moiety is one of those that leads to a product of type 2 with tin-containing compounds, then the factors operating in the formation of both type 2 and type 3 compounds become involved, and reaction with an acid or salt containing a heteropolyanion of composition $M'_{11}XO_{39}$ gives a polymeric product (type 6) that can be represented by the formula $$\{[Q^+]_a[L_{b\text{-}1}MGe_2M'_{11}XO_{40}]^{a-}\}_y, \quad (6)$$

or more simply as $(Q_aL_{b\text{-}1}MGe_2M'_{11}XO_{40})_y$. The terms in these formulas are defined as for formula (1), and the considerations noted for formula (1) again apply. The value of y, the degree of polymerization, can be of the order of up to about 500. The actual repeating unit in the polymeric structure is the novel heteropolyanionic moiety $L_{b\text{-}1}MGe_2M'_{11}XO_{40}$. A cationic moiety $Q_a$ is associated with each such heteropolyanionic moiety, but the latter moieties are bonded directly to each other, not through the $Q_a$ moieties. Suitable products of type 6 include $\{[(CH_3)_3NH]_5(CO)_3CoGe_2W_{11}SiO_{40}\}_y$.

The products of the invention can undergo ligand-displacement reactions, in which one or more L ligands are replaced by other types of L ligands to give different products of the invention. An illustrative preparative reaction of this type is shown in Example 26.

BEST MODE

The following examples illustrate the products of the invention. All temperatures are in °C.

Starting materials not available commercially were prepared as follows:

$K_8W_{11}SiO_{39}$ Hydrate $Na_4W_{12}SiO_{40}$ hydrate (13 g) in water (40 ml) was heated to 90°. A solution of potassium acetate (15 g) in water (20 ml) was brought to pH 7.0 with acetic acid, heated to 90° and added to the first solution. The mixture was stirred for five minutes at 90° and then filtered hot. The solid on the filter was 12.75 g of $K_8W_{11}SiO_{39}\cdot10H_2O$. Part of a lot prepared similarly but on a larger scale was analyzed:

| Anal. Calcd for $K_8W_{11}SiO_{39} \cdot 10H_2O$: K, 9.88; Si, 0.88; O, 24.75; W, 63.85; $H_2O$, 5.69 | | | | | |
|---|---|---|---|---|---|
| Found: | K, | 10.0; | Si, | 0.55; | O, 24.41; W, 63.14; |
| | | 9.6 | | 0.52 | |
| | | | | 0.86 | |
| | | | | 0.88 | |
| | $H_2O$, | 5.87 | | | |
| | | 5.87 | | | |

In some preparations tungstosilicic acid was used in place of its sodium salt with no significant difference in the result.

$(CO)_4CoSnCl_3$

This was prepared by two methods. The first is described by Patmore and Graham, Inorg. Chem., 7, 771 (1968). The second is mentioned, without details, by Ogino and Brown, Inorg. Chem., 10, 517 (1971). The following procedure was developed based on the brief mention by Ogino and Brown and is the preferred method because of higher yield.

Sodium amalgam was prepared from 99 g of mercury and sodium (1 g) in a nitrogen atmosphere. Tetrahydrofuran (200 ml) was added, followed by dicobalt octacarbonyl (6.85 g). The mixture was stirred for three hours. The resulting tetrahydrofuran solution was decanted from the mercury and filtered. The filter cake was rinsed down into the original filtrate with additional tetrahydrofuran. Triphenyltin chloride (15.4 g) was added to the filtrate and the mixture was stirred overnight. It was then filtered. The filtrate was evaporated to dryness and the residue was stirred in tin tetrachloride (25 ml) for thirty minutes. This mixture was filtered. The filtrate was concentrated on a rotary evaporator in vacuum at ambient temperature until it was thick with a precipitate of a yellow crystalline solid. This was isolated by filtration, rinsed twice with hexane and dried to obtain 6.24 g of $(CO)_4CoSnCl_3$. Recrystallization from hexane gave 3.5 g recovery of this product in two crops. Both the recrystallized and the unrecrystallized products prepared in this fashion are suitable for use in the reactions described herein.

"$\pi$-$C_5H_5Fe(CO)_2SnCl_3$"

One literature reference (Manning, Chem. Comm., 906 (1966) states that the reaction of $\pi$-$C_5H_5Fe(CO)_2I$ with excess $SnCl_2.2H_2O$ in methanol forms $\pi$-$C_5H_5Fe(CO)_2SnCl_2I.CH_3OH$, while a more recent report by Mays and Pearson, J. Chem. Soc. (A), 136 (1969), says this is incorrect and that the product, which is said to precipitate from the reaction mixture, is $\pi$-$C_5H_5Fe(CO)_2SnCl_3$. It was found that this reaction gives a methanol-soluble species which has a chlorine:iodine ratio of 10:1. This product is suitable for use in the process of this invention as a source of the $\pi$-$C_5H_5(CO)_2Sn$- moiety and is referred to herein in quotation marks, "$\pi$-$C_5H_5Fe(CO)_2SnCl_3$", to reflect the uncertainty in its structure.

A mixture of commercially available $\pi$-$C_5H_5$-$Fe(CO)_2I$ (10 g), methanol (250 ml) and $SnCl_2.2H_2O$ (75 g) was refluxed for eight hours in a nitrogen atmosphere and then let cool and stand for twelve hours. It was filtered to remove a small amount of dark solid and obtain an orange filtrate. The slow addition of water to this filtrate caused the separation of 10.8 g of "$\pi$-$C_5H_5Fe(CO)_2SnCl_3$" as a crystalline orange solid.

| Anal. Calcd for $C_5H_5Fe(CO)_2SnCl_3$: C, 20.91; | | | | | | |
|---|---|---|---|---|---|---|
| H, 1.25; Cl, 26.46; Fe, 13.89; I, 0.0; Sn, 29.52 | | | | | | |
| Found: | C, | 16.77; | H, | 1.65; | Cl, 23.76; | Fe, 11.02; |
|  |  | 16.89 |  | 1.51 | 23.25 | 11.03 |
|  | I, | 8.34; | Sn, | 30.00 |  |  |
|  |  | 8.26 |  | 30.32 |  |  | p-$FC_6H_4Pt[P(C_2H_5)_3]_2SnCl_3$ was prepared as described by Parshall, J. Am. Chem. Soc., 88, 704 (1966).

$\pi$-$C_5H_5W(CO)_3SnCl_3$ is described by Bonati and Wilkinson, J. Chem. Soc., 179 (1964). The material used in the present work was prepared by a different route:

a. A mixture of sodium cyclopentadienide (10.6 g), tetrahydrofuran (200 ml) and tungsten hexacarbonyl (35.5 g) was refluxed overnight in a nitrogen atmosphere and cooled. A solution of acetic acid (7.2 g) in tetrahydrofuran (200 ml) was added and the mixture was stripped to dryness. The residue was sublimed at 50° in vacuum to obtain 8.2 g of $\pi$-$C_5H_5W(CO)_3H$. This was stirred for one hour in carbon tetrachloride and filtered to obtain 7.1 g of $\pi$-$C_5H_5W(CO)_3Cl$.

b. A mixture of anhydrous stannous chloride (29 g) and $\pi$-$C_5H_5W(CO)_3Cl$ (2.7 g) in diethylene glycol dimethyl ether (40 ml) was refluxed in a nitrogen atmosphere for two hours and then allowed to cool and stand overnight. It was then filtered in air. The major portion of the filtrate was evaporated in a rotary evaporator under vacuum to leave a residual oil. The oil was mixed with ethanol (25 ml), causing the separation of crystalline orange $\pi$-$C_5H_5W(CO)_3SnCl_3$ (1.2 g, dec 182°, lit mp 187° (Bonati and Wilkinson)).

$Cl_3SnFe(CO)_3NO$ was prepared by the method of Casey and Manning, Chem. Comm., 674, (1970), with slight modification as reported here.

Tin tetrachloride (6 g) was added to $Hg[Fe(CO)_3NO]_2$ (7.7 g) in 100 ml of toluene in a dry nitrogen atmosphere and stirred several hours. The mixture was filtered. Slight concentration of the filtrate caused precipitation of 2.75 g of $Cl_3SnFe(CO)_3NO$ as an orange red crystalline solid which was rinsed three times with hexane and dried. An additional 5.38 g was obtained by evaporating the filtrate to dryness. Both crops of product had infrared spectra which agreed with that reported for $Cl_3SnFe(CO)_3NO$ by Casey and Manning.

$Cl_3SnFe(CO)_2(P(C_6H_5)_3)NO$ was prepared according to Casey and Manning, J. Chem. Soc., (A), 256 (1971), except that toluene was used as solvent instead of benzene.

$Co_2W_{11}O_{39}.H_2O^{7-}$

This anion was prepared according to Baker and McCutcheon, J. Am. Chem. Soc., 78, 4503 (1956). That paper described the isolation of an ammonium salt of $[Co^{+2}Co^{+3}W_{12}O_{42}]^{-7}$ (anion II in that paper). This characterization was erroneous and the formulation of the anion was later (Baker et al, J. Am. Chem. Soc., 88, 2329 (1966)) corrected to $[H_2Co^{+2}O_6Co^{+3}O_4W_{11}O_3]^{-7}$ (anion 4 in the latter paper) which is identical to $Co_2W_{11}O_{39}.H_2O^{7-}$. The preparation given in the original paper was followed except that the product anion was isolated by a tetramethylammonium salt.

Acetic acid (40 ml) was added to a solution of sodium tungstate (198 g) in 400 ml of water, bringing the pH to 7.1. A solution of cobaltous acetate tetrahydrate (24.9 g) in water (125 ml) plus five drops of acetic acid was added. The solution was boiled for ten minutes and filtered hot. The filtrate was heated to 80° and ammonium persulfate (15 g) was added slowly. After the addition was complete, the mixture was boiled for ten minutes and then cooled. The addition of tetramethylammonium chloride precipitated a dark brown solid which was used as the starting material in Example 16.

$\pi$-$C_5H_5Fe(CO)_2GeCl_3$ was prepared as described by Edmondson, Eisner, Newlands and Thompson, J. Organometal. Chem., 35, 119 (1972).

$(C_6H_5)_3P(\pi$-$C_3H_5)PdSnCl_3$ was prepared according to Mason et al., Chem. Commun., 1655 (1968).

$[(C_6H_5)_3P]_2Ir(CO)(H)_2SnCl_3$ was prepared by the method of Taylor, Young and Wilkinson, Inorg. Chem., 5, 20 (1966).

EXAMPLE 1

$[(CH_3)_4N]_5(CO)_4CoSnW_{11}SiO_{39}$ $Cl_3SnCo(CO)_4$ (0.5 g, 1.3 mmoles) was added to a mixture of $K_8W_{11}SiO_{39}.10H_2O$ (3.0 g, 0.95 mmoles) and water (10 ml). The mixture was heated to 60° briefly and filtered hot. Tetramethylammonium chloride in excess was added to the filtrate, precipitating a light blue solid. Part of this (1.3 g) was recrystallized from a mixture of ethanol (20 ml) and water (23 ml). The solid dissolved completely while the mixture was hot, forming a clear light yellow solution. This was allowed to cool but was filtered while still warm to separate 0.1 g of a yellow solid. The filtrate from this separation was allowed to cool to ambient temperature and stand for two hours. Filtration then gave a light pink solid, A. The filtrate from the isolation of A was heated to 75° and diluted with ethanol until it became cloudy. On cooling, this solution separated additional solid, B, which was identical with A by infrared analysis. The combined weight of A and B was 0.5 g. Solid A was analyzed and found to contain $[(CH_3)_4N]_5(CO)_4CoSnW_{11}SiO_{39}.12H_2O$.

| Anal. Calcd for [(CH$_3$)$_4$N]$_5$(CO)$_4$CoSnW$_{11}$SiO$_{39}$ . 12H$_2$O: | | | | | | | |
|---|---|---|---|---|---|---|---|
| | C, | 8.12; | H, | 2.38; | N, 1.97; | Co, | 1.66; |
| | O, | 24.78; | Sn, | 3.34 | | | |
| Found: | C, | 7.36; | H, | 1.97; | N, 1.89; | Co, | 1.12; |
| | | 7.36 | | 2.00 | 1.82 | | 1.10 |
| | O, | 24.36; | Sn, | 2.43 | | | |
| | | | | 2.56 | | | |

The presence of a significant amount of water was confirmed by infrared analysis; the infrared spectrum also included bands at about 2110, 2050, 2020 and 2000 cm$^{-1}$, consistent with the above formula.

EXAMPLE 2

[(CH$_3$)$_3$NH]$_{11}$(CO)$_3$Co(SnW$_{11}$SiO$_{39}$)$_2$

H$_{11}$(CO)$_3$Co(SnW$_{11}$SiO$_{39}$)$_2$

A. A solution of Cl$_3$SnCo(CO)$_4$ (4.0 g, 10.1 mmoles) in tetrahydrofuran (30 ml) was added to a solution of K$_8$W$_{11}$SiO$_{39}$.10H$_2$O (20 g, 6.3 mmoles) in water (150 ml) at 70°. The mixture was stirred at 70° for 15 minutes, cooled to ambient temperature and filtered. The filtrate was stripped to dryness; the residue was dissolved in water (40 ml). Excess trimethylammonium chloride was added to precipitate a gray-green solid which was recrystallized from 285 ml of water which contained trimethylammonium chloride (4 g), then from 80 ml of water and finally from another 80 ml of water. The final product was dried at ambient temperature in vacuum overnight to obtain 9.89 g of a hydrate of [(CH$_3$)$_3$NH]$_{11}$(CO$_3$)-Co(SnW$_{11}$SiO$_{39}$)$_2$ as a golden-yellow crystalline solid. Part of this was dried at 140° in vacuum overnight before analysis.

| Anal. Calcd for [(CH$_3$)$_3$NH]$_{11}$(CO)$_3$Co(SnW$_{11}$SiO$_{39}$)$_2$-.4H$_2$O: | | | | | | | | | |
|---|---|---|---|---|---|---|---|---|---|
| | C, | 6.69; | H, | 1.86; | N, | 2.38; | O, | 21.04; | |
| | Co, | 0.91; | Sn, | 3.67; | Si. | 0.87; | W, | 62.57; | |
| | H$_2$O, | 1.11 | | | | | | | |
| Found: | C, | 6.74; | H, | 1.83; | N, | 2.30; | O, | 20.89; | |
| | | 6.85 | | 1.90 | | 2.34 | | 21.16 | |
| | Co, | 0.86; | Sn, | 3.47; | Si, | 0.74; | W, | 62.94; | H$_2$O, 1.27 |
| | | 0.87 | | 3.45 | | 0.74 | | 62.62 | 1.24 |

The infrared spectrum (mineral-oil mull) included a weak C≡O band at 2022 cm$^{-1}$ and stronger ones at 1959 and 1947 cm$^{-1}$, consistent with the above formula. The ultraviolet spectrum in 0.01 N H$_2$SO$_4$, determined on a sample prepared in similar fashion to the above, had $\lambda_{max}$ 259 m$\mu$ ($\epsilon$ 80,000) and $\lambda_{max}$ 319 m$\mu$ ($\epsilon$99,700).

B. A solution of [(CH$_3$)$_3$NH]$_{11}$(CO)$_3$Co(SnW$_{11}$SiO$_{39}$)$_2$.4H$_2$O (1.5087 g) in warm water (150 ml) was passed through an ion-exchange column containing 15 g of a strongly acidic ion-exchange resin [crosslinked poly(styrenesulfonic acid) type]. The column was rinsed until the rinsings were no longer acidic. The original effluent and the rinsings were combined to obtain an aqueous solution of H$_{11}$(CO)$_3$Co(SnW$_{11}$SiO$_{39}$)$_2$. The pH of this dilute solution was 2.05. Titration with 0.1 N sodium hydroxide gave a titration curve typical of a strong acid; all protons appeared to be of equivalent strength. The observed neutral equivalent was 612; the calculated neutral equivalent (based on the amount of [(CH$_3$)$_3$NH]$_{11}$(CO)$_3$Co(SnW$_{11}$SiO$_{39}$)$_2$.4H$_2$O used) is 588. The titration data suggest that nucleophilic decomposition of the anion starts at about pH 7.

In a similar ion-exchange experiment with 1.5 g of the same salt, 100 ml of warm water and 20 ml of the same ion exchange resin, the acidic effluent was evaporated to leave a green gum which redissolved in water to give a yellow solution. The green gum was hydrated H$_{11}$(CO)$_3$Co(SnW$_{11}$SiO$_{39}$)$_2$.

EXAMPLE 3

K$_{11}$(CO)$_3$Co(SnW$_{11}$SiO$_{39}$)$_2$

A solution of [(CH$_3$)$_3$NH]$_{11}$(CO)$_3$Co(SnW$_{11}$SiO$_{39}$)$_2$ (11.5 g) in warm water (400 ml) was passed through an ion-exchange column containing 35 ml of the potassium salt of a crosslinked poly(styrenesulfonic acid) resin. The combined effluent and column rinsings were evaporated to dryness and the residue was further dried at 140° in vacuum overnight to leave a hydrate of K$_{11}$(CO)$_3$Co(SnW$_{11}$SiO$_{39}$)$_2$ as a dark-brown solid. The infrared spectrum of the solid was consistent with this formula.

EXAMPLE 4

Na$_{11}$(CO)$_3$Co(SnW$_{11}$SiO$_{39}$)$_2$

A solution of [(CH$_3$)$_3$NH]$_{11}$(CO)$_3$Co(SnW$_{11}$SiO$_{39}$)$_2$ (205 g) in warm (40° C.) water (5 liters) was passed through an ion-exchange column containing 1500 ml of a crosslinked poly(styrenesulfonic acid) resin which had largely been converted to a sodium salt beforehand with solutions of sodium acetate and sodium hydroxide. The effluent and rinsings were combined and found to have a pH of 3. They were brought to pH 6.4–6.5 with aqueous sodium hydroxide and evaporated to dryness to leave a solid hydrate of Na$_{11}$(CO)$_3$Co(SnW$_{11}$SiO$_{39}$)$_2$. It was found preferable to use dilute (0.1 N to 0.2 N) sodium hydroxide solution for the final neutralization rather than concentrated sodium hydroxide solution because the latter can cause some decomposition of the anion due to temporary local overbasification even with good stirring.

EXAMPLE 5

[(CH$_3$)$_3$NH]$_9$(CO)$_3$Co(SnW$_{11}$PO$_{39}$)$_2$

A solution of lithium acetate (20 g) in water (30 ml) was adjusted to pH 5.5 with acetic acid and added to a solution of tungstophosphoric acid (21 g, 6.9 mmoles) in water (70 ml) at 70° followed immediately by a solution of Cl$_3$SnCo(CO)$_4$(4.0 g, 10.1 mmoles) in tetrahydrofuran (20 ml). An immediate red color formed; the temperature was maintained at 70° for 5 minutes and the mixture was then filtered. The filtrate was allowed to cool and was refiltered. Trimethylammonium chloride in excess was added to the major portion of the filtrate to precipitate a solid, which was recrystallized three times from water, first from 100 ml. then from 80 ml and finally from 50 ml, to obtain a golden-yellow crystalline solid which was a hydrate of [(CH$_3$)$_3$NH]$_9$[(CO)$_3$-Co(SnW$_{11}$PO$_{39}$)$_2$] (1.7 g). This was dried at ambient temperature in vacuum.

| Anal. Calcd for [(CH$_3$)$_3$NH]$_9$(CO)$_3$Co(SnW$_{11}$PO$_{39}$)$_2$-.12H$_2$O: | | | | | | | | |
|---|---|---|---|---|---|---|---|---|
| | C, | 5.55; | H, | 1.77; | N, | 1.94; | O, | 22.80; |
| | Co, | 0.91; | Sn, | 3.66; | W, | 62.30; | H$_2$O, | 3.32 |
| Found: | C, | 6.38; | H, | 1.60; | N, | 2.01; | O, | 21.00; |
| | | 6.24 | | 1.56 | | 2.09 | | 20.81 |
| | Co, | 0.93; | Sn, | 3.71; | W, | 64.02; | H$_2$O; | 3.64 |
| | | 0.93 | | 3.68 | | 64.42 | | 3.52 |

The infrared spectrum included a weak C≡O absorption band at 2031 cm$^{-1}$ and stronger ones at 1971 and 1950 cm$^{-1}$, consistent with the assigned formulation.

If the foregoing process is essentially repeated, using tungstogermanic acid in place of tungstophosphoric acid, hydrated [(CH$_3$)$_3$NH]$_{11}$(CO)$_3$Co(SnW$_{11}$GeO$_{39}$)$_2$ will be obtained.

EXAMPLE 6

K$_9$(CO)$_3$Co(SnW$_{11}$PO$_{39}$)$_2$

An aqueous solution of [(CH$_3$)$_3$NH]$_9$(CO)$_3$Co(SnW$_{11}$PO$_{39}$)$_2$ was passed through an ion-exchange column containing an excess of the potassium salt of a crosslinked poly(styrenesulfonic acid) cation exchange resin. Evaporation of the effluent left 4.76 of a hydrate of K$_9$(CO)$_3$Co(SnW$_{11}$PO$_{39}$)$_2$. The ultraviolet spectrum in 0.01 N H$_2$SO$_4$, determined on a sample prepared in similar fashion to the above, had $\lambda_{max}$ 258 m$\mu$ (k=13.6), 314 m$\mu$ (k=10.0).

EXAMPLE 7

[(CH$_3$)$_3$NH]$_5$$\pi$-C$_5$H$_5$Fe(CO)$_2$SnW$_{11}$SiO$_{39}$

A solution of "$\pi$-C$_5$H$_5$Fe(CO)$_2$SnCl$_3$" (3.0 g, ca. 7.5 mmoles) in methanol (30 ml) was added to a solution of K$_8$W$_{11}$SiO$_{39}$.10H$_2$O (12.7 g, 4.0 mmoles) in water (90 ml). The mixture was heated to 60° and maintained at this temperature for five minutes. It was then cooled and filtered. Excess trimethylammonium chloride was added to the filtrate to precipitate an orange solid, which was recrystallized from water. The recrystallized [(CH$_3$)$_3$NH]$_5$$\pi$-C$_5$H$_5$Fe(CO)$_2$SnW$_{11}$SiO$_{39}$ (7.8 g) was dried at 140° overnight before analysis.

| Anal. Calcd for [(CH$_3$)$_3$NH]$_5$C$_5$H$_5$Fe(CO)$_2$SnW$_{11}$SiO$_{39}$: | | | | | | | | | |
|---|---|---|---|---|---|---|---|---|---|
| | C, | 8.08; | H, | 1.68; | N, | 2.14; | Fe, | 1.71; | |
| | O, | 20.06; | Si. | 0.86; | Sn, | 3.63; | W, | 61.83; | |
| | H$_2$O, | 0.0 | | | | | | | |
| Found: | C, | 8.31; | H, | 1.73; | N, | 2.08; | Fe, | 1.57; | |
| | | 8.02 | | 1.71 | | 2.09 | | 1.59 | |
| | O, | 20.80; | Si, | 0.88; | Sn, | 3.50; | W, | 61.82 | |
| | | 20.48 | | 0.84 | | 3.48 | | 61.43 | |
| | H$_2$O, | 0.24 | | | | | | | |
| | | 0.26 | | | | | | | |

The infrared spectrum (mineral-oil mull) displayed C≡O stretching absorption frequencies at 2013 and 1961 cm$^{-1}$. The ultraviolet spectrum, determined in 0.01 N H$_2$SO$_4$ had $\lambda_{max}$ 260 m$\mu$ ($\epsilon$ 43,200), 418 (sh) ($\epsilon$ 540). The proton nmr spectrum included resonances due to CH$_3$-N and C$_5$H$_5$ protons in an integrated area ratio of 10.7:1, compared with a calculated ratio of 9:1.

If $\pi$-C$_5$H$_5$Ru(CO)$_2$SnCl$_3$ is substituted for "$\pi$-C$_5$H$_5$Fe(CO)$_2$SnCl$_3$" in essentially the foregoing process, [(CH$_3$)$_3$NH]$_5$$\pi$-C$_5$H$_5$Ru(CO)$_2$SnW$_{11}$SiO$_{39}$ will be obtained. If (dimethylglyoxime)$_2$Co(NC$_5$H$_5$)CoSnCl$_3$ is used in place of "$\pi$-C$_5$H$_5$Fe(CO)$_2$SnCl$_3$", the product will be [(CH$_3$)$_3$NH]$_5$(dimethylglyoxime)$_2$Co(NC$_5$H$_5$)CoSnW$_{11}$SiO$_{39}$.

EXAMPLE 8

K$_5$$\pi$-C$_5$H$_5$Fe(CO)$_2$SnW$_{11}$SiO$_{39}$

A solution of [(CH$_3$)$_3$NH]$\pi$-C$_5$H$_5$Fe(CO)$_2$SnW$_{11}$SiO$_{39}$ (14.15 g) in warm water (100 ml) was passed through an ion-exchange column containing 45 ml of the potassium salt of a crosslinked poly(styrenesulfonic acid) cation-exchange resin. The column was rinsed down with water; the rinsings and the original effluent were combined and evaporated to dryness to leave 13.7 g of a hydrate of K$_5$$\pi$-C$_5$H$_5$Fe(CO)$_2$SnW$_{11}$SiO$_{39}$.

EXAMPLE 9

[(CH$_3$)$_4$N]$_5$p-FC$_6$H$_4$Pt[P(C$_2$H$_5$)$_3$]$_2$SnW$_{11}$SiO$_{39}$

A solution of p-FC$_6$H$_4$Pt[P(C$_2$H$_5$)$_3$]$_2$SnCl$_3$ (2.9 g, 3.9 mmoles) in tetrahydrofuran (15 ml) was added to a solution of K$_8$W$_{11}$SiO$_{39}$.10H$_2$O (9.0 g, 2.8 mmoles) in water (75 ml) which had been heated to 50°. The mixture was stirred at 50°–54° for four minutes and filtered before cooling. Tetramethylammonium chloride was added to a major portion of the filtrate to precipitate a white solid, which was separated by filtration from a yellow liquid. The proton nmr spectrum of the precipitate included resonances due to CH$_3$-N, C$_2$H$_5$-P and p-FC$_6$H$_4$Pt protons in intensity ratios of 63:28:3.7, compared to 60:30:4 calculated for the formulation [(CH$_3$)$_4$N]$_5$p-FC$_6$H$_4$Pt[P(C$_2$H$_5$)$_3$]$_2$SnW$_{11}$SiO$_{39}$. This precipitate was recrystallized from 60 ml of 50% aqueous acetone and dried at ambient temperature in vacuum overnight and then at 80° in vacuum overnight to obtain a hexahydrate of the above salt.

| Anal. Calcd for [(CH$_3$)$_4$N]$_5$FC$_6$H$_4$Pt[P(C$_2$H$_5$)$_3$]$_2$SnW$_{11}$SiO$_{39}$ . 6H$_2$O: | | | | | | | | | |
|---|---|---|---|---|---|---|---|---|---|
| | C, | 12.02; | H, | 2.81; | N, | 1.84; | O, | 18.95; | |
| | Si, | 0.74; | Sn, | 3.12; | W, | 53.24; | H$_2$O, | 2.89. | |
| Found: | C, | 12.13; | H, | 2.54; | N, | 1.99; | O, | 17.83; | |
| | | 12.12 | | 2.68 | | 1.90 | | 17.97 | |
| | Si, | 0.87; | Sn, | 3.10; | W, | 53.76; | H$_2$O, | 2.89 | |
| | | 0.82 | | 3.13 | | 53.60 | | 2.89 | |

If p-FC$_6$H$_4$Pt[P(C$_2$H$_5$)$_3$]$_2$SnCl$_3$ is replaced by C$_6$H$_5$Pt[P(C$_2$H$_5$)$_3$]$_2$SnCl$_3$ and K$_8$W$_{11}$SiO$_{39}$.10H$_2$O is replaced by K$_8$W$_{11}$GeO$_{39}$ hydrate in essentially the foregoing process, [(CH$_3$)$_4$N]$_5$C$_6$H$_5$Pt[P(C$_2$H$_5$)$_3$]$_2$SnW$_{11}$GeO$_{39}$ hydrate will be obtained.

EXAMPLE 10

[(CH$_3$)$_3$NH]$_4$$\pi$-C$_5$H$_5$Fe(CO)$_2$SnW$_{11}$PO$_{39}$

A solution of lithium acetate (15 g) in water (20 ml) was brought to pH 7 with acetic acid and added to a solution of tungstophosphoric acid (12 g, ca. 3.9 mmoles) in water (60 ml) at 60° followed rapidly by a solution of "$\pi$-C$_5$H$_5$Fe(CO)$_2$SnCl$_3$" (3.5 g, ca. 8.7 mmoles) in methanol (20 ml). The reaction temperature was maintained at 60° for five minutes. The mixture was then filtered twice. Trimethylammonium chloride was added to the filtrate to precipitate a yellow solid, which was recrystallized from water (100 ml) and then digested briefly in boiling water (50 ml). It was then dried in vacuum at room temperature to obtain 4.1 g of the trihydrate of [(CH$_3$)$_3$NH]$_4$[$\pi$-C$_5$H$_5$Fe(CO)$_2$SnW$_{11}$PO$_{39}$].

| Anal. Calcd for [(CH$_3$)$_3$NH]$_4$C$_5$H$_5$Fe(CO)$_2$SnW$_{11}$PO$_{39}$ . 3H$_2$O: | | | | | | | | | |
|---|---|---|---|---|---|---|---|---|---|
| | C, | 6.98; | H, | 1.57, | N, | 1.71; | O, | 21.54; | Fe, 1.71; |
| | | | Sn, | 3.63; | W, | 61.89; | H$_2$O; | 1.65 | |
| Found: | C, | 7.05; | H, | 1.51; | N, | 1.74; | O, | 20.21; | |
| | | 7.06 | | 1.48 | | 1.67 | | 21.26 | |
| | | | | | | | | 20.48 | |
| | Fe, | 1.76; | Sn, | 3.66; | W, | 61.95; | H$_2$O, | 1.89 | |
| | | 1.80 | | 3.65 | | 62.16 | | 1.92 | |

The proton nmr spectrum displays a $CH_3$-$N$:$C_5H_5$ proton ratio of 7.5:1 compared to a calculated value of 7.2:1. The infrared spectrum determined in a mineral-oil mull includes $C\equiv O$ absorption bands at 2021 and 1971 $cm^{-1}$. The ultraviolet spectrum, determined in 0.01 N $H_2SO_4$ on a sample prepared in a fashion similar to that described above, had a maximum at 260 m$\mu$ ($\epsilon$ 99,300) with a shoulder at 410 m$\mu$ ($\epsilon$ 621).

If "$\pi$-$C_5H_5Fe(CO)_2SnCl_3$" is replaced by $\pi$-$C_5H_5Ni(CO)SnCl_3$ and tungstophosphoric acid is replaced by tungstogermanic acid in essentially the foregoing process, $[(CH_3)_3NH]_5\pi$-$C_5H_5Ni(CO)SnW_{11}GeO_{39}$ or a hydrate thereof will be obtained.

EXAMPLE 11

$K_4\pi$-$C_5H_5Fe(CO)_2SnW_{11}PO_{39}$

A solution of $[(CH_3)_3NH]_4\pi$-$C_5H_5Fe(CO)_2SnW_{11}PO_{39}$ (18 g) in hot water (250 ml) was passed through an ion-exchange column containing 55 ml of the potassium salt of a crosslinked poly(styrenesulfonic acid) cation-exchange resin. The column was rinsed down with water. The combined original effluent and rinsings were evaporated to dryness to leave 17.4 g of a solid hydrate of $K_4\pi$-$C_5H_5Fe(CO)_2SnW_{11}PO_{39}$.

EXAMPLE 12

$[(CH_3)_4N]_5\pi$-$C_5H_5W(CO)_3SnW_{11}SiO_{39}$

A solution of $\pi$-$C_5H_5W(CO)_3SnCl_3$ (1.1 g, 2.0 mmoles) in tetrahydrofuran (15 ml) was added to a solution of $K_8W_{11}SiO_{39}$.$10H_2O$ (5.0 g, 1.6 mmoles) in water (50 ml) which had been heated to 70°. The mixture was stirred at 70° for five minutes and then filtered. The addition of excess tetramethylammonium chloride to the filtrate caused precipitation of a gray solid. This was dissolved in boiling water (30 ml) which was allowed to cool to ambient temperature. A mixture of gray and lighter-colored solids was obtained. This mixture, still in the 30 ml of water, was reheated to redissolve the solids. The solution was allowed to cool until the gray solid had crystallized and was then filtered. The filtrate was reheated and filtered again while hot to obtain a small amount of an insoluble solid and an orange filtrate. The filtrate was allowed to cool; a cream colored, almost light yellow solid separated. This was dried at ambient temperature in vacuum and found to comprise 2.5 g of $[(CH_3)_4N]_5\pi$-$C_5H_5W(CO)_3SnW_{11}SiO_{39}$.$6H_2O$.

| Anal. Calcd for $[(CH_3)_4N]_5C_5H_5W(CO)_3SnW_{11}SiO_{39}$. $6H_2O$: | | | | | | | | | |
|---|---|---|---|---|---|---|---|---|---|
| | C, | 9.32; | H, | 2.15; | N, | 1.94; | O, | 21.30; | |
| | Si. | 0.78; | Sn, | 3.29; | W, | 61.20; | $H_2O$, | 3.00. | |
| Found: | C, | 9.99; | H, | 2.10; | N, | 2.12; | O, | 20.48; | |
| | | 9.82 | | 2.06 | | 2.0 | | 20.75 | |
| | Si, | 0.89; | Sn, | 3.27; | W, | 61.10; | $H_2O$, | 3.33 | |
| | | 0.87 | | 3.31 | | 61.60 | | 3.37 | |

The proton nmr spectrum displayed a $CH_3N$:$C_5H_5$ proton ratio of 13.5:1 compared to a calculated ratio of 12:1. The infrared spectrum, determined in a mineral-oil mull, included a $C\equiv O$ absorption based at 2015 $cm^{-1}$ and one at 1911 $cm^{-1}$ with a shoulder at about 1945 $cm^{-1}$.

If $\pi$-$C_5H_5W(CO)_3SnCl_3$ is replaced by $\pi$-$C_5H_5Mo(CO)_2P(C_6H_5)_3SnI_3$ in essentially the foregoing process, a hydrate of $[(CH_3)_4N]_5\pi$-$C_5H_5Mo(CO)_2P(C_6H_5)_3SnW_{11}SiO_{39}$ will be obtained.

EXAMPLE 13

$[(CH_3)_3NH]_{11}(CO)_2Fe(NO)(SnW_{11}SiO_{39})_2$ $Cl_3SnFe(CO)_3NO$ (2.75 g, 7.0 mmoles) was added to methanol (10 ml). There was immediate gas evolution. After this had subsided, the now dark-red solution was added to a solution of $K_8W_{11}SiO_{39}$.$10H_2O$ (9.0 g, 2.84 mmoles) in water (60 ml) at 60°. The mixture was stirred for five minutes at 60° and then filtered at this temperature. Trimethylammonium chloride was added to the major portion of the reaction mixture to precipitate a solid which was recrystallized two times, 60 ml of water being used each time. The hot solution was filtered through diatomaceous earth during the second crystallization. A crystalline yellow solid (3.6 g) was obtained which was dried at room temperature in vacuum to obtain $[(CH_3)_3NH]_{11}(CO)_2Fe(NO)(SnW_{11}SiO_{39})_2$.$7H_2O$.

| Anal. Calcd for $[(CH_3)_3NH]_{11}(CO)_2Fe(NO)$-$(SnW_{11}SiO_{39})_2$ . $7H_2O$: | | | | | | | | | |
|---|---|---|---|---|---|---|---|---|---|
| | C, | 6.45; | H, | 1.92; | N, | 2.58; | O, | 21.60, | Fe, |
| | | 0.88; | Si, | 0.86; | Sn, | 3.64; | W, | 62.08; | $H_2O$, |
| | | 1.93. | | | | | | | |
| Found: | C, | 6.45; | H, | 1.70; | N, | 2.56; | O, | 20.10; | |
| | | 6.46 | | 1.62 | | 2.59 | | 20.08 | |
| | Fe, | 0.88; | Si, | 0.90; | Sn, | 3.59, | W, | 62.29 | |
| | | 0.86 | | 0.87 | | 3.50 | | 62.04 | |
| | $H_2O$, | 1.86 | | | | | | | |
| | | 1.92 | | | | | | | |

The infrared spectrum, determined in a mineral-oil mull, displayed $C\equiv O$ stretching absorption bands at 1980 and 1930 $cm^{-1}$ and an absorption for the NO group at 1730 $cm^{-1}$. The ultraviolet spectrum, determined in 0.01 N $H_2SO_4$ on a sample prepared in a similar fashion, had a maximum at 260 m$\mu$ ($\epsilon$ 79,300).

If $K_8W_{11}SiO_{39}$.$10H_2O$ is replaced by $K_7W_{11}PO_{39}$ in essentially the foregoing process, the product obtained will be $[(CH_3)_3NH]_9(OC)_2Fe(NO)[SnW_{11}PO_{39}]_2$ hydrate.

EXAMPLE 14

$K_{11}(CO)_2Fe(NO)(SnW_{11}SiO_{39})_2$

A solution of $[(CH_3)_3NH]_{11}(CO)_2Fe(NO)SnW_{11}SiO_{39})_2$ (20.9 g) in water (1 liter) was passed through an ion-exchange column containing 90 ml of the potassium salt of a crosslinked poly(styrenesulfonic acid) cation-exchange resin. The effluent was evaporated to dryness to leave a solid hydrate of $K_{11}(OC)_2Fe(NO)(SnW_{11}SiO_{39})_2$.

EXAMPLE 15

$K_8(CO)_3Co(SnO_3)SnW_{11}PO_{39}$

A. Potassium cyanide was added to an aqueous solution of $K_9(CO)_3Co(SnW_{11}PO_{39})_2$ at room temperature. A yellow solid precipitated immediately. The infrared spectrum of this solid, later shown to be a hydrate of $K_8(CO)_3Co(SnO_3)SnW_{11}PO_{39}$ (see below), had absorption bands for $C\equiv O$ resembling those in the starting heteropolyanion, $K_9(CO)_3Co(SnW_{11}PO_{39})_2$, but was much more opaque at 900-700 $cm^{-1}$.

B. Potassium cyanide (1.0 g) was added to a solution of $K_9(CO)_3Co(SnW_{11}PO_{39})_2$ (2.0 g) in water (10 ml). The yellow solid which separated was removed by filtration and washed with water six times. It was dried at 80° in vacuum to obtain 0.7 g of $K_8(OC)_3Co($ SnO$_3$)SnW$_{11}$PO$_{39}$.12H$_2$O, which can also be formulated as K$_5$(CO)$_3$Co[Sn(OK)$_3$]SnW$_{11}$PO$_{39}$.12H$_2$O.

| Anal. Calcd for K$_8$(CO)$_3$Co( SnO$_3$)SnW$_{Sn}$W$_{11}$PO$_{39}$ | | | | | | | | | | |
|---|---|---|---|---|---|---|---|---|---|---|
| | C, | 0.99; | H, | 0.67; | N, | 0.00; | C, | 25.09; | Co, | 1.62; |
| | K, | 8.60; | Sn, | 6.53; | W, | 55.64; | H$_2$O, | 5.94 | | |
| Found: | C, | 0.78; | H, | 0.46; | N, | 0.1; | O, | 23.90; | | |
| | | 0.75 | | 0.20 | | 0.1 | | | | |
| | Co, | 1.57; | K, | 8.49; | Sn, | 6.24; | W, | 55.72; | | |
| | | 1.57 | | 8.40 | | 6.14 | | 55.28 | | |
| | H$_2$O, | 5.73 | | | | | | | | |
| | | 5.76 | | | | | | | | |

EXAMPLE 16

[(CH$_3$)$_4$N]$_7$π-C$_5$H$_5$Fe(CO)$_2$SnW$_{11}$CoO$_{39}$

A solution of lithium acetate (10 g) in water (20 ml) was brought to pH 6.5 with acetic acid, heated to 50° and then added to a solution of the dark-brown solid which was prepared as described earlier (12.8 g) in water (30 ml) which had been heated to 50°. This was followed immediately by the addition of a solution of "π-C$_5$H$_5$Fe(CO)$_2$SnCl$_3$" (2 , ca. 5 mmoles) in methanol (15 ml) which had been heated to 50°. The mixture was then warmed to 60° and stirred at this temperature for fifteen minutes. It was filtered while still hot; the filtrate was refiltered after it had cooled to obtain a dark blue filtrate to which was added tetramethylammonium chloride. A small amount of dark blue solid separated and was removed by filtration. The filtrate was concentrated in stages with precipitated solids being removed between stages. This was continued until the infrared spectrum of the solid isolated included substantial carbonyl absorption bands (at ca 2010 and 1960 cm$^{-1}$). This fraction (A) was a crystalline dark green solid (2.2 g). The filtrate from the isolation of this solid was concentrated further and a portion of the concentrate was diluted with methanol to precipitate 0.6 g of a green solid (B). This had an infrared spectrum almost identical with that of fraction A except that the relative intensity of the carbonyl absorption bands in the spectrum of B was slightly greater than in the spectrum of A, implying that B was slightly more pure than A.

| Anal. Calcd for [(CH$_3$)$_4$N]$_7$C$_5$H$_5$Fe(CO)$_2$SnW$_{11}$CoO$_{39}$: | | | | | | | | |
|---|---|---|---|---|---|---|---|---|
| | C, | 11.94; | H, | 2.55; | N, | 2.79; | Co, | 1.67; |
| | Fe, | 1.59; | Sn, | 3.37. | | | | |
| Found: | | | C, | 11.51; | H, | 3.26; | N, | 2.42; |
| ('B'): | | | | 1.48 | | 3.00 | | 2.37 |
| | Co, | 1.79; | Fe, | 1.17; | Sn, | 2.80 | | |
| | | 1.78 | | 1.16 | | 2.74 | | |

If (n-C$_4$H$_9$)$_3$PCo(CO)$_3$SnCl$_3$ is used in place of "π-C$_5$H$_5$Fe(CO)$_2$SnCl$_3$", the product will be [(CH$_3$)$_4$N]$_7$(n-C$_4$H$_9$)$_3$PCo(CO)$_3$SnW$_{11}$CoO$_{39}$.

EXAMPLE 17

[(CH$_3$)$_4$N]$_5$(CO)$_2$Fe(NO)[P(C$_6$H$_5$)$_3$]SnW$_{11}$SiO$_{39}$

A solution of K$_8$W$_{11}$SiO$_{39}$.10H$_2$O (2.3 g, 7.3 mmoles) in water (150 ml) was heated to 50°. A solution of (CO)$_2$Fe(NO)[P(C$_6$H$_5$)$_3$]SnCl$_3$ (5.7 g, 7.3 mmoles) in tetrahydrofuran (50 ml) was added and the reaction mixture was stirred and heated at 50°–60° for thirty minutes. The major portion of the reaction mixture was filtered; the addition of tetramethylammonium chloride to the filtrate precipitated a yellow solid, which was recrystallized from 900 ml of water. The recrystallization filtrate was allowed to cool and the liquid portion, which contained a finely divided suspended yellow solid, was decanted from the bulk of the solid, which had settled to the bottom of the vessel. The latter solid was then isolated and dried at ambient temperature in vacuum overnight to obtain 7.2 g of [(CH$_3$)$_4$N]$_5$(CO)$_2$Fe(NO)[P(C$_6$H$_5$)$_3$]SnW$_{11}$SiO$_{39}$.5H$_2$O.

| Anal. Calcd for [(CH$_3$)$_4$N]$_5$(CO)$_2$Fe(NO)[P(C$_6$H$_5$)$_3$]- | | | | | | | | |
|---|---|---|---|---|---|---|---|---|
| SnW$_{11}$SiO$_{39}$ . 5H$_2$O: | | | | | | | | |
| | C, | 13.13; | H, | 2.34; | N, | 2.30; | O, | 20.55; Fe, |
| | 1.53; | Sn, | 3.24; | W, | 55.29; Si, | 0.77; | | |
| | H$_2$O, | 2.46 | | | | | | |
| Found: | C, | 11.13; | H, | 2.02; | N, | 1.94; | C, | 20.01; |
| | | 11.27 | | 2.01 | | 1.95 | | 19.94 |
| | Fe, | 1.36; | Sn, | 2.56; | W, | Si, | 0.83; | |
| | | | | | | 56.83; | | |
| | | 1.34 | | 2.53 | | 56.25 | 0.77 | |
| | H$_2$O, | 2.66 | | | | | | |
| | | 2.65 | | | | | | |

The proton nmr spectrum displayed a methyl:aryl ratio of 4.4:1, compared to a calculated ratio of 4:1. The infrared spectrum, determined in a mineral-oil mull, included C≡O absorption bands at about 2040 and 1960 cm$^{-1}$ and an NO absorption band at about 1755 cm$^{-1}$.

If (C$_6$H$_5$O)$_3$PFe(CO)$_2$(NO)SnCl$_3$ is used in place of (OC)$_2$Fe(NO)P(C$_6$H$_5$)$_3$SnCl$_3$ and K$_8$W$_{11}$GeO$_{39}$ hydrate is used in place of K$_8$W$_{11}$SiO$_{39}$.10H$_2$O in essentially the preceding process, the product will be [(CH$_3$)$_4$N]$_5$(C$_6$H$_5$O)$_3$PFe(CO)$_2$(NO)SnW$_{11}$GeO$_{39}$.

EXAMPLE 18

[(CH$_3$)$_3$NH]$_4$(π-C$_5$H$_5$Fe(CO)$_2$Ge)$_2$W$_{11}$SiO$_{40}$

A solution of π-C$_5$H$_5$Fe(CO)$_2$GeCl$_3$ (4.3 g, 12.1 mmoles) in methanol (30 ml) was added to a solution of K$_8$W$_{11}$SiO$_{39}$.10H$_2$O (25 g, 7.89 mmoles) in water (180 ml) at 60°. The mixture was stirred at 60° for ten minutes to obtain a clear orange solution. This was filtered and excess trimethylammonium chloride was added to the filtrate, precipitating a yellow solid. This was isolated by filtration, washed with water and dried overnight at ambient temperature in vacuum. The yield at this point was 26.23 g. Five grams of this was recrystallized from 450 ml of water. The yellow solid recovered from the recrystallization was dried at ambient temperature overnight to obtain 1.6 g of [(CH$_3$)$_3$NH]$_4$(π-C$_5$H$_5$Fe(CO)$_2$Ge)$_2$W$_{11}$SiO$_{40}$. The infrared spectrum of the crude product was nearly identical with that of the recrystallized solid and included strong C≡O absorption bands at ca. 1990 and 2040 cm$^{-1}$.

| Anal. Calcd for [(CH$_3$)$_3$NH]$_4$(C$_5$H$_5$Fe(CO)$_2$Ge)$_2$- | | | | | | | | |
|---|---|---|---|---|---|---|---|---|
| W$_{11}$SiO$_{40}$: | | | | | | | | |
| | C, | 9.10; | H, | 1.46; | N, | 1.63; | O, | 20.52; |
| | K, | 0.0; | Fe, | 3.24; | Ge, | 4.23; | Si, | 0.82; |
| | W, | 58.96; | H$_2$O, | 0.0. | | | | |
| Found: | C, | 9.03; | H, | 1.53; | N, | 1.61; | O, | 20.51; |

| | | | | | | | |
|---|---|---|---|---|---|---|---|
| | 9.06 | | | 1.53 | | 1.61 | 20.44 |
| K, | 0.0; | Fe, | 3.30; | 3.30 | Ge, | 3.77; 3.84 | Si, 1.02 | 1.03; |
| W, | 57.53; 57.25 | H₂O, | 0.16 0.25 | | | | |

The proton nmr spectrum had a $CH_3$-$N$:$C_5H_5$ proton ratio of 3.5:1 compared to a calculated ratio of 3.6:1.

EXAMPLE 19

$[(CH_3)_3NH]_3[\pi\text{-}C_5H_5Fe(CO)_2Ge]_2W_{11}PO_{40}$

A solution of lithium acetate (15 g) in water (20 ml) was brought to pH 7 with acetic acid and then added to a solution of tungstophosphoric acid (11 g, 3.6 mmoles) in water (60 ml) which had been heated to 60°. A solution of $\pi$-$C_5H_5Fe(CO)_2GeCl_3$ (2.74 g, 7.7 mmoles) in methanol (15 ml) was added and the mixture was heated to 60° briefly. It was filtered to obtain a small amount of yellow solid and a yellow filtrate. An aliquot of this filtrate was mixed with trimethylammonium chloride to precipitate an almost white solid. The infrared spectrum of this solid had very weak carbonyl (C≡O) absorption bands. The yellow solid from the first filtration was dissolved in methanol (15 ml) and added to the remainder of the original yellow filtrate. The resulting solution was heated to boiling (90°) briefly. An aliquot of this solution was mixed with tetramethylammonium chloride to precipitate a white solid which was not investigated further. The remainder of the yellow filtrate was brought to pH 3.8 by the dropwise addition of concentrated hydrochloric acid. The color became a much deeper yellow orange during this addition. Excess trimethylammonium chloride was added, precipitating a bright-yellow solid. The infrared spectrum of this solid, determined in a mineral-oil mull, had strong C≡O absorption bands at ca. 2050 and 2000 cm⁻¹. The proton nmr spectrum had a $CH_3$-$N$:$C_5H_5$ proton ratio of 2.67:1 compared to a ratio of 2.7:1 calculated for $[(CH_3)_3NH]_3(\pi\text{-}C_5H_5Fe(CO)_2Ge)_2W_{11}PO_{40}$. The 5.7 g of this solid that was obtained was recrystallized from 550 ml of water to obtain 4.9 g of recrystallized yellow $[(CH_3)_3NH]_3(\pi\text{-}C_5H_5Fe(CO)_2Ge)_2W_{11}PO_{40}$.

| Anal. Calcd for $[(CH_3)_3NH]_3[C_5H_5Fe(CO)_2Ge]_2$-$W_{11}PO_{40}$: | | | | | | | |
|---|---|---|---|---|---|---|---|
| | C, | 8.20; | H, | 1.05; | N, | 1.25; | O, 20.90; |
| | Fe, | 3.32; | Ge, | 4.31; 3.95 | | | |
| Found: | C, | 8.27; 8.24 | H, | 1.18; 1.17 | N, | 1.25; 1.20 | O, 20.36; 20.21 19.66 |
| | Fe, | 3.42; 3.50 | Ge, | 3,.87; | H₂O, | 0.46 0.46 | |

If the above process is repeated in its essentials, but replacing $\pi$-$C_5H_5Fe(CO)_2GeCl_3$ with the species listed in column A, and the tungstophosphoric acid with the species in column B, the corresponding product in column C will be obtained.

| A | B | C |
|---|---|---|
| $(C_6H_5)_3PCo(CO)_3$-$GeCl_3$ | Unchanged | $[(CH_3)_3NH]_3$-$[(C_6H_5)_3PCo(CO)_3$-$Ge]_2W_{11}PO_{40}$ |
| $(C_6H_5)_3AsCo$-$(CO)_3GeCl_3$ | Tungstosilic Acid | $[(CH_3)_3NH]_4$-$[(C_6H_5)_3AsCo(CO)_3$-$Ge]_2W_{11}SiO_{40}$ |
| $\pi$-$C_5H_5Ni[P(C_2$-$H_5)_3]GeCl_3$ | Tungstogermanic Acid | $[(CH_3)_3NH]_4$-$[\pi$-$C_5H_5(C_2H_5)_3$-$PNiGe]_2W_{11}GeO_{40}$ |

EXAMPLE 20

$[(CH_3)_3S]_4(H)\pi\text{-}C_5H_5Fe(CO)_2SnMo_{11}SiO_{39}$

A solution of potassium acetate (30 g) in water (40 ml) was adjusted to pH 5 with acetic acid and added to a solution of $Na_4Mo_{12}SiO_{40}$ (15 g, ca. 7.5 mmole) in water (100 ml). The resulting mixture was heated to 50° and a solution of "$\pi$-$C_5H_5Fe(CO)_2SnCl_3$" (5.02 g, ca. 12.5 mmoles) in methanol (40 ml) was added. The reaction mixture was then stirred at 50° for five minutes and filtered. Trimethylsulfonium iodide (excess) was added to the dark-yellow-brown filtrate to precipitate a brown solid. This was stirred in boiling water (100 ml) and the solution was filtered hot; the filtrate was refiltered after it had cooled slightly to remove the initial solid that separated. It was then allowed to cool and stand overnight at room temperature. Filtration gave a yellow-brown solid which was dried at ambient temperature in vacuum to obtain 4.5 g of $[(CH_3)_3S]_4(H)\pi$-$C_5H_5Fe(CO)_2SnMo_{11}SiO_{39}\cdot4H_2O$.

| Anal. Calcd for $[(CH_3)_3S]_4(H)C_5H_5Fe(CO)_2SnMo_{11}$-$SiO_{39}\cdot4H_2O$: | | | | | | | | | |
|---|---|---|---|---|---|---|---|---|---|
| | C, | 9.56; | H, | 2.11; | S, | 5.38; | O, | 30.19; | |
| | Fe, | 2.33; | Si, | 1.18; | Sn, | 4.98; | Mo, | 44.26; | |
| | H₂O, | 3.02 | | | | | | | |
| Found: | C, | 9.77; 9.81 9.74 9.90 | H, | 1.83; 1.81 2.07 2.07 | S, | 5.99; 5.89 | O, | 28.31; 28.59 | |
| | Fe, | 2,24; 2.30 | Si, | 1.43; 1.37 | Sn, | 4.88; 4.86 | Mo, | 45.43; 45.37 | |
| | H₂O, | 3.47 3.29 | | | | | | | |

The proton nmr spectrum had a $CH_3$-$S$:$C_5H_5$ proton ratio of 8.25:1 compared to 7.2:1 calculated. The infrared spectrum, determined in a mineral oil mull, included C≡O absorption bands at ca. 2040 and 1980 cm⁻¹. An aqueous slurry of the compound had a pH of 4.0, consistent with its formulation as an acid salt.

If the foregoing process is repeated in its essentials but replacing "$\pi$-$C_5H_5Fe(CO)_2SnCl_3$" with the reagents listed in Column A, the corresponding products in Column B will be obtained.

| A | B |
|---|---|
| $\pi$-$C_5H_5Mo(CO)_2P(OCH_3)_3SnCl_3$ | $[(CH_3)_3S]_4(H)\pi$-$C_5H_5Mo$-$(CO)_2P(OCH_3)_3SnMo_{11}SiO_{39}$ |
| $\pi$-$C_5H_5Ru(CO)_2SnCl_3$ | $[(CH_3)_3S]_4(H)\pi$-$C_5H_5Ru$-$(CO)_2SnMo_{11}SiO_{39}$ |
| $[(C_6H_5)_2PCH_2CH_2P$-$(C_6H_5)_2]_2Re(CO)SnCl_3$ | $[(CH_3)_3S]_4(H)[(C_6H_5)_2PCH_2$-$CH_2P(C_6H_5)_2]_2Re(CO)$-$SnMo_{11}SiO_{39}$ |

EXAMPLE 21

$[(CH_3)_4N]_{10}SnW_{11}SiO_{39}Co(CO)_3SnW_{11}PO_{39}$

A mixture of $K_5(CO)_3Co[Sn(OK)_3]SnW_{11}PO_{39}$ (0.7 g) (Example 18 B) and water (30 ml) was brought to pH 4.9 by the addition of three drops of glacial acetic acid.

$K_8W_{11}SiO_{39}.10H_2O$ (0.64 g) was added with stirring. The mixture was heated to 60° to obtain a clear orange solution, pH 6.12, which was cooled to ambient temperatue. The addition of tetramethylammonium chloride precipitated an orange solid. This was recrystallized from a small amount of dilute aqueous tetramethylammonium chloride to obtain 0.81 g of $[(CH_3)_4N]_{10}SnW_{11}SiO_{39}Co(CO)_3SnW_{11}PO_{39}$.

| Anal. Calcd for $[(CH_3)_4N]_{10}SnW_{11}SiO_{39}Co(CO)_3$-$SnW_{11}PO_{39}$: | | | | | | | | |
|---|---|---|---|---|---|---|---|---|
| | C, | 7.98; | H, | 1.87; | N, | 2.16; | Co, | 0.91; |
| | Si, | 0.43; | Sn, | 3.67 | | | | |
| Found: | C, | 8.12; | H, | 1.97; | N, | 2.21; | Co, | 1.06; |
| | | 8.32 | | 2.00 | | 2.19 | | 1.15 |
| | Si, | 0.70; | Sn, | 4.54 | | | | |
| | | 0.69 | | 4.57 | | | | |

The infrared spectrum includes absorption bands for C≡O, P-O, and Si-O moieties.

If this process is repeated, but using molybdosilicic acid (which degrades to $Mo_{11}SiO_{39}{}^{8-}$ at the pH specified) in place of $K_8W_{11}SiO_{39}.10H_2O$, the product will be $[(CH_3)_4N]_{10}SnW_{11}SiO_{39}Co(CO)_3SnMo_{11}SiO_{39}$.

EXAMPLE 22

$[(CH_3)_3NH]_4\pi\text{-}C_5H_5Co(CO)(GeOH)_2W_{11}SiO_{39}$

A solution of $\pi\text{-}C_5H_5Co(CO)(GeCl_3)_2$ (1.02 g) in warm methanol (10 ml) was added to a solution of $K_8W_{11}SiO_{39}.10H_2O$ (3.2 g) in water (20 ml) at 60°. The mixture was stirred for ten minutes at 50°-60° and then filtered. The addition of trimethylammonium chloride to the yellow filtrate precipitated a yellow solid, which was recrystallized from water to obtain 1.1 g of $[(CH_3)_3NH]_4\pi\text{-}C_5H_5Co(CO)(GeOH)_2W_{11}SiO_{39}.3H_2O$.

| Anal. Calcd for $[(CH_3)_3NH]_4C_5H_5Co(CO)(GeOH)_2$-$W_{11}SiO_{39} . 3H_2O$: | | | | | | | | |
|---|---|---|---|---|---|---|---|---|
| | C, | 6.55; | H, | 1.62; | N, | 1.70; | O, | 21.82; |
| | Co, | 1.79; | Ge, | 4.40; | $H_2O$, | 1.64 | | |
| Found: | C, | 6.76; | H, | 1.42; | N, | 1.68; | O, | 19.82; |
| | | 6.78 | | 1.51 | | 1.68 | | 20.08 |
| | Co, | 2.16; | Ge, | 5.20; | $H_2O$, | 1.82 | | |
| | | 2.16 | | 5.16 | | 1.67 | | |

The infrared spectrum displays C≡O stretching absorption at about 2080 cm$^{-1}$; the proton nmr spectrum shows the presence of methyl and cyclopentadienyl protons in a 7.1:1 ratio (calc'd 7.2:1).

If the foregoing process is repeated but replacing $\pi\text{-}C_5H_5Co(CO)[GeCl_3]_2$ with the reagent in column A and $K_8W_{11}SiO_{19}$ with the reagent in column B, the product in column C will be obtained.

| A | B | C |
|---|---|---|
| $\pi\text{-}C_5H_5Co(CO)\text{-}(GeBr_3)_2$ | $K_8W_{11}GeO_{39}$ | $[(CH_3)_3NH]_4\pi C_5H_5\text{-}Co(CO)(GeOH)_2\text{-}W_{11}GeO_{39}$ |
| $(C_6H_5NC)_2Pd\text{-}(GeCl_3)_2$ | $K_7W_{11}PO_{39}$ | $[(CH_3)_3NH]_3\text{-}(C_6H_5NC)_2Pd\text{-}(GeOH)_2W_{11}PO_{39}$ |

EXAMPLE 23

$[(CH_3)_3NH]_4(C_7H_8)_2RhSnW_{11}PO_{39}$

A solution of lithium acetate (15 g) in water (80 ml) was adjusted to pH 6 with acetic acid. Tungstophosphoric acid (11 g) was added; the pH was then 5.0. Solid $(C_7H_8)_2RhSnCl_3$ (1.8 g; $C_7H_8$=norbornadiene) was added and the mixture was stirred for several minutes at ambient temperature and then filtered. The addition of trimethylammonium chloride to the dark-red filtrate precipitated a rust-colored solid. This was recrystallized from water to obtain 8.9 g of $[(CH_3)_3NH]_4(C_7H_8)_2RhSnW_{11}PO_{39}.H_2O$ (after drying in vacuum at ambient temperature).

| Anal. Calcd for $[(CH_3)_3NH]_4(C_7H_8)_2RhSnW_{11}\text{-}PO_{39} . H_2O$: | | | | | | | | |
|---|---|---|---|---|---|---|---|---|
| | C, | 9.34; | H, | 1.75; | N, | 1.68; | O, | 19.15; |
| | Rh, | 3.08; | Sn, | 3.55; | $H_2O$, | 0.54; | | |
| Found: | C, | 9,38; | H, | 1.73; | N, | 1.57; | O, | 18.83 |
| | | 9.36 | | 1.68 | | 1.56 | | 19.11 |
| | Rh, | 2.75; | Sn, | 3.55; | $H_2O$, | 0.82 | | |
| | | 2.79 | | 3.45 | | 0.84 | | |

The proton nmr spectrum was consistent with the above formula.

If the foregoing process is repeated, replacing the $(C_7H_8)_2RhSnCl_3$ with the reagent in column A and the tungstophosphoric acid with the reagent in column B, the product in column C will be obtained:

| A | B | C |
|---|---|---|
| $(C_7H_8)_2IrSnCl_3$ | Tungstosilicic Acid | $[(CH_3)_3NH]_5\text{-}(C_7H_8)_2IrSn\text{-}W_{11}SiO_{39}$ |
| $(Ph_3As)_2(C_8H_{12})\text{-}IrSnCl_3$ | Tungstogermanic Acid | $[(CH_3)_3NH]_5(Ph_3\text{-}As)_2C_8H_{12}IrSn\text{-}W_{11}GeO_{39}$ |
| $C_7H_8Co(CO)_2\text{-}SnCl_3$ | Tungstosilicic Acid | $[(CH_3)_3NH]_5\text{-}C_7H_8Co(CO)_2Sn\text{-}W_{11}SiO_{39}$ |

EXAMPLE 24

$[(CH_3)_3NH]_5\pi\text{-}C_5H_5Fe(CO)_2SnW_{11}GeO_{39}$

12-Tungstogermanic acid (12 g, Polysciences, Inc.) was added to a solution of lithium acetate (15 g) in water (60 ml) after the solution had been brought to pH 5.5 by the addition of acetic acid. The resulting mixture (pH 5.2) was heated to 50° and a warm solution of "$\pi\text{-}C_5H_5Fe(CO)_2SnCl_3$" (3 g) in warm methanol (35 ml) was added. The reaction mixture was then heated at 60°-70° for five minutes and filtered. The addition of trimethylammonium chloride precipitated a yellow-brown solid which was recrystallized two times from water. The product from the second recrystallization was collected in two fractions. The first fraction was obtained by filtration after the hot recrystallization had been allowed to cool normally for two hours. The filtrate from this separation was reheated to boiling, allowed to cool for three hours and then filtered to obtain a second fraction, which consisted of 0.55 g of yellow $[(CH_3)_3NH]_5\pi\text{-}C_5H_5Fe(CO)_2SnW_{11}GeO_{39}$. This was dried at ambient temperature in vacuum overnight before analysis.

| Anal. Calc'd for $[(CH_3)_3NH]_5C_5H_5Fe(CO)_2Sn\text{-}W_{11}GeO_{39}$: | | | | | | | |
|---|---|---|---|---|---|---|---|
| | C, | 7.97; | H, | 1.67; | N, | 2.11; | Fe, | 1.68; |
| | Ge, | 2.19; | Sn, | 3.58 | | | | |
| Found: | C, | 7.92; | H, | 1.57; | N, | 1.90; | Fe, | 1.75; |
| | | 7.97 | | 1.57 | | 1.93 | | 1.74 |

| | | | | | | |
|---|---|---|---|---|---|---|
| | Ge, | 2.02; | Sn, | 3.56 | | |
| | | 1.98 | | 3.56 | | |

The proton nmr spectrum exhibited $C_5H_5$ and $CH_3$ resonances in an integral ratio of 1:9.1 (Calc'd 1:9).

EXAMPLE 25

$\{[(CH_3)_3NH]_5(CO)_3CoGe_2W_{11}SiO_{40}\}_y$

A solution of $(CO)_4CoGeCl_3$ (7.0 g, 20 mmoles) in tetrahydrofuran (30 ml) was added, in a nitrogen atmosphere, to a solution of $K_8W_{11}SiO_{39}\cdot 10H_2O$ (20 g, 6.3 mmoles) at 60°–65°. The reaction mixture was heated 15 minutes in this temperature range and then filtered through sintered glass and then through pre-wet filter paper. Excess trimethylammonium chloride was added to the filtrate. Filtration then gave a dark-brown solid plus a blue filtrate. The solid was extracted with 50 ml of boiling water in air; part of the solid (A) did not dissolve. The dark-blue extract was filtered hot, the filtrate was allowed to cool to 40°–45° and filtered at this temperature to obtain a yellow solid (B), which was rinsed three times with small portions of water. The infrared spectrum of B confirmed that it had an $(CO)_3Co$ rather than an $(CO)_4Co$ moiety. The infrared spectrum of A was similar to that of B. The approximate amounts of A and B obtained were 1.6 and 1.0 g, respectively. Analysis of B was consistent with the formulation $[(CH_3)_3NH]_5(CO)_3CoGe_2W_{11}SiO_{40}$.

| Anal. Calc'd for $[(CH_3)_3NH]_5(CO)_3CoGe_2W_{11}SiO_{40}$: | | | | | | | | |
|---|---|---|---|---|---|---|---|---|
| | C, | 6.59; | H, | 1.53; | N, | 2.13; | O, | 20.98; |
| | Co, | 1.80; | Ge, | 4.42; | Si, | 0.86 | | |
| Found: | C, | 6.37; | H, | 1.36; | N, | 2.24; | O, | 21.39; |
| | | 6.18 | | 1.66 | | 2.19 | | 20.49 |
| | | | | | | | | 20.76 |
| | Co, | 1.92; | Ge, | 4.03; | Si, | 0.93 | | |
| | | 1.91 | | 4.02 | | 0.91 | | |

Bonding considerations require that the anion $(OC)_3CoGe_2W_{11}SiO_{40}^{5-}$ actually be polymeric, $[(OC)_3CoGe_2W_{11}SiO_{40}^{5-}]_y$. A small amount of A was dissolved in hot water. A gel formed as the solution cooled, which is also consistent with a polymeric structure for the product. Analysis by light scattering indicated a molecular weight of about $10^6$, corresponding to a value of y of about 330.

EXAMPLE 26

$[(CH_3)_3NH]_4[(C_6H_5)_3P]_2(C_7H_8)RhSnW_{11}PO_{39}$ $[(CH_3)_3NH]_4(C_7H_8)_2RhSnW_{11}PO_{39}$ (3.0 g; Ex. 23) was heated in refluxing acetonitrile (100 ml). Water was added slowly until a clear solution formed. This required 25 ml of water. Triphenylphosphine (1.5 g) was added. The solution became dark brown immediately and a brown-red solid separated within a minute. Refluxing was continued for 8 minutes; the mixture was then filtered while still hot. The solid was dried overnight at ambient temperature in vacuum. It was washed thoroughly with methylene chloride and re-dried. The yield was 2.7 g. Proton nmr analysis was consistent with the $[(CH_3)_3NH]_4[(C_6H_5)_3P]_2(C_7H_8)RhSnW_{11}PO_{39}$ formulation; the spectrum displayed aryl, bridgehead, olefinic, methyl and methylene protons in ratios 15:1:1.7:17:0.7 compared to calculated ratios of 15:1:2:18:1.

| Anal. Calc'd for $[(CH_3)_3NH]_4[(C_6H_5)_3P]_2C_7H_8$-$RhSnW_{11}PO_{39}$: | | | | | | | | |
|---|---|---|---|---|---|---|---|---|
| | C, | 17.58; | H, | 2.09; | N, | 1.49; | O, | 16.61; |
| | Rh, | 2.74; | Sn, | 3.26; | $H_2O$, | 0.0 | | |
| Found: | C, | 18.20; | H, | 2.23; | N, | 1.41; | O, | 16.02; |
| | | 18.07 | | 2.25 | | 1.43 | | 15.74 |
| | Rh, | 0.93; | Sn, | 3.12; | $H_2O$, | 0.49 | | |
| | | 1.10 | | 3.05 | | | | |

EXAMPLE 27

$[(CH_3)_3NH]_{11}\pi\text{-}C_3H_5Pd(SnW_{11}SiO_{39})_2$ $[(CH_3)_3NH]_5(C_6H_5)_3P(\pi\text{-}C_3H_5)PdSnW_{11}SiO_{39}$ A. A solution of $(C_6H_5)_3P(\pi\text{-}C_3H_5)PdSnCl_3$ (3.0 g) in tetrahydrofuran (30 ml) was prepared in a nitrogen atmosphere and then added in air to a solution of $K_8W_{11}SiO_{39}\cdot 10H_2O$ (10.5 g) in water (75 ml) at 60°. The mixture was maintained at 60° for ten minutes, allowed to cool, and filtered. The filtrate was diluted with water (50 ml) and refiltered through diatomaceous earth. Excess trimethylammonium chloride was added to the filtrate to precipitate a near-white solid. This mixture was filtered to isolate an off-white solid (A) and obtain a yellow filtrate, from which 2.3 g of bright-yellow crystalline $[(CH_3)_3NH]_{11}\pi\text{-}C_3H_5Pd(SnW_{11}SiO_{39})_2$ slowly separated.

| Anal. Calc'd for $[(CH_3)_3NH]_{11}C_3H_5Pd(SnW_{11}SiO_{39})_2$: | | | | | | | | |
|---|---|---|---|---|---|---|---|---|
| | C, | 6.76; | H, | 1.81; | N, | 2.40; | O, | 19.5; |
| | Pd, | 1.66; | Si, | 0.88; | Sn, | 3.71 | | |
| Found: | C, | 6.79; | H, | 1.82; | N, | 2.28; | O, | 18.71; |
| | | 6.72 | | 1.89 | | 2.29 | | |
| | Pd, | 1.74; | Si, | 0.93; | Sn, | 3.73 | | |
| | | 1.71 | | 0.92 | | 3.68 | | |

Proton nuclear magnetic resonance analysis confirmed the presence of the allyl group and the absence of triphenylphosphine. The allyl:methyl proton ratio was correct for the above composition.

B. The process of part A was repeated except that it was conducted entirely in a nitrogen atmosphere. This did not appear to change the results. The off-white solid (6.0 g) corresponding to solid A in the preceding reaction was analyzed and found to be a mixture of approximately one-third $[(CH_3)_3NH]_{11}\pi\text{-}C_3H_5Pd(SnW_{11}SiO_{39})_2$ and two-thirds $[(CH_3)_3NH]_5(C_6H_5)_3P(\pi\text{-}C_3H_5)PdSnW_{11}SiO_{39}$.

| Anal. Calc'd for mixture as specified: C, 10.46; | | | | | | |
|---|---|---|---|---|---|---|
| H, 1.94; N, 2.13; Pd, 2.57; Sn, 3.50 | | | | | | |
| Found: | C, | 10.65; | H, | 2.05; | N, | 2.10; Pd, 2.49; |
| | | 10.94 | | 2.08 | | 2.15  2.43 |
| | Sn, | 3.53 | | | | |
| | | 3.58 | | | | |

Proton nmr analysis of this mixture revealed a phenyl:allyl:methyl group ratio of 2.2:0.9:21 compared with 2:1:21 calculated for the mixture.

Other palladium-containing compounds similar to the first product of the foregoing example can be made by suitable variations in the procedure described therein. These include $H_9\pi\text{-}C_3H_5Pd(SnW_{11}PO_{39})_2$, $Na_{11}\pi\text{-}C_3H_5Pd(SnW_{11}GeO_{39})_2$, and $K_{11}\pi\text{-}C_3H_5Pd(SnMo_{11}SiO_{39})_2$.

EXAMPLE 28

[(CH$_3$)$_3$NH]$_4$[$\pi$-C$_5$H$_5$Fe(CO)$_2$Ge]$_2$Mo$_{11}$SiO$_{40}$

A solution of lithium acetate (12 g) in water (100 ml) was brought to pH 5.5 with acetic acid. Fifteen grams of Na$_4$Mo$_{12}$SiO$_{40}$ hydrate was added. The solution was stirred for ten minutes and then filtered. The filtrate was warmed to 55° and a warm solution of $\pi$-C$_5$H$_5$Fe(CO)$_2$GeCl$_3$ (7.0 g) in methanol (45 ml) was added. The solution was then heated to 60° and allowed to cool. The major portion of the reaction mixture was then filtered, allowed to stand for thirteen days, and refiltered. Trimethylammonium chloride (0.5 g) was added to the filtrate to precipitate a greenish-yellow solid. The major portion of this was washed with water at ambient temperature and then dried overnight in vacuum at room temperature. It consisted of 1.2 g of [(CH$_3$)$_3$NH]$_4$[$\pi$-C$_5$H$_5$Fe(CO)$_2$Ge]$_2$Mo$_{11}$SiO$_{40}$.

| Anal. Calc'd for [(CH$_3$)$_3$NH]$_4$[$\pi$-C$_5$H$_5$Fe(CO)$_2$Ge]$_2$Mo$_{11}$SiO$_{40}$: | | | | | | | | |
|---|---|---|---|---|---|---|---|---|
| | C, | 12.68; | H, | 2.05; | N, | 2.27; | Fe, | 4.53; |
| | Ge, | 5.89; | O, | 28.58 | | | | |
| Found: | C, | 11.92; | H, | 1.87; | N, | 2.03; | Fe, | 5.26; |
| | | 12.11 | | 1.94 | | 2.00 | | 4.84 |
| | Ge, | 6.04; | O, | 28.46 | | | | |
| | | 5.85 | | 29.19 | | | | |
| | | | | 28.59 | | | | |

The proton nmr spectrum had a methyl-to-cyclopentadienyl proton ratio of 4.2:1 (calc'd for above salt: 3.6:1). The infrared spectrum was consistent with the formulation, exhibiting C≡O and molybdosilicate absorption bands.

EXAMPLE 29

K$_5$[(C$_6$H$_5$)$_3$P]$_2$Ir(CO)(H)$_2$SnW$_{11}$SiO$_{39}$

A solution of [(C$_6$H$_5$)$_3$P]$_2$Ir(CO)(H)$_2$SnCl$_3$ (0.97 g) in tetrahydrofuran (10 ml) was added to a solution of K$_8$W$_{11}$SiO$_{39}$.10H$_2$O (3.2 g) in water (40 ml) at 60° C. The resulting mixture was stirred for 45 minutes and then filtered. The filter cake was extracted with water (150 ml) at 55° C. The filtered extracts were allowed to cool and were then mixed with a solution of potassium nitrate (1.0 g) in water (10 ml). After thirty minutes another one gram of potassium nitrate in water (10 ml) was added. After two more hours the mixture was filtered to obtain a hydrate of K$_5$[(C$_6$H$_5$)$_3$P]$_2$Ir(CO)(H)$_2$SnW$_{11}$SiO$_{39}$. The remainder of the original filter cake was then reextracted with boiling water (100 ml). The filtered extracts were mixed with a solution of potassium nitrate (2.0 g) in water (15 ml), allowed to stand for two hours and refiltered. This gave more of the same product obtained above. The combined yield was 1.5 g.

| Anal. Calc'd for K$_5$[(C$_6$H$_5$)$_3$P]$_2$Ir(CO)(H)$_2$SnW$_{11}$SiO$_{39}$ . 6 H$_2$O: | | | | | | | | |
|---|---|---|---|---|---|---|---|---|
| | C, | 11.56; | H, | 1.15; | K, | 5.09; | Sn, | 3.09 |
| Found: | C, | 12.35; | H, | 1.32; | K, | 5.14; | Sn, | 3.54 |
| | | 11.77 | | 1.35 | | 4.95 | | 3.66 |

The infrared spectrum, determined in a mineral-oil mull, exhibited absorptions at 2120 cm$^{-1}$ (Ir-H) and 2010 cm$^{-1}$ (C≡O) as well as bands characteristic of water, coordinated triphenylphosphine, and the —SnW$_{11}$SiO$_{39}$ moiety. The proton nmr spectrum had resonances for the aromatic and for the hydride protons in an observed ratio of 17.2:1, compared to a calculated ratio of 15:1. The hydridic protons exhibited one resonance at 21.2 $\tau$ (J$_{P-H(cis)}$=15 cps; J$_{H-H}$=4 cps) and one of equal intensity at 22 $\tau$ (J$_{P-H(trans)}$=108 cps; J$_{P-H(cis)}$=15 cps; J$_{H-H}$=4 cps).

The use of [(C$_6$H$_5$)$_3$P]$_2$Ir(CO)(D)$_2$SnCl$_3$, prepared according to the reference given above, in place of [(C$_6$H$_5$)$_3$P]$_2$Ir(CO)(H)$_2$SnCl$_3$ in a similar experiment gave the corresponding deuteride.

EXAMPLE 30

[(CH$_3$)$_3$NH]$_5$[(C$_2$H$_5$)$_3$P]$_2$Pt(H)SnW$_{11}$SiO$_{39}$

A solution of K$_8$W$_{11}$SiO$_{39}$.10H$_2$O (9.5 g) in water (75 ml) was prepared and heated to 60°–65°. A solution of 2.1 g of trans-[(C$_2$H$_5$)$_3$P]$_2$Pt(H)SnCl$_3$; Lindsey, Parshall, and Stolberg, J. Am. Chem. Soc., 87, 658 (1967); in tetrahydrofuran (15 ml) was added. The mixture was stirred for five minutes at 65° and then filtered while still hot. Excess trimethylammonium chloride was added to the yellow filtrate to precipitate a yellowish-green solid (8.0 g). The infrared spectrum (mineral-oil mull) of this solid had an absorption band at about 2090 cm$^{-1}$, demonstrating retention of the Pt-H moiety. Part of this solid (5.4 g) was stirred in water (300 ml) at 40°–45° to obtain a turbid solution which was filtered through diatomaceous earth. Successive additions of trimethylammonium chloride to the filtrate, each addition followed by filtration, gave three successive crops of yellow solid. The last crop was analyzed.

| Anal. Calc'd for [(CH$_3$)$_3$NH]$_5$[(C$_2$H$_5$)$_3$P]$_2$Pt(H)SnW$_{11}$SiO$_{39}$: | | | | |
|---|---|---|---|---|
| | Pt, | 5.53; | Sn, | 3.37 |
| Found: | Pt, | 4.91; | Sn, | 3.19 |
| | | 5.13 | | 3.12 |

EXAMPLE 31

[(CH$_3$)$_3$NH]$_4$[(C$_2$H$_5$)$_3$P]$_2$Pt(H)SnW$_{11}$PO$_{39}$

A solution of lithium acetate (15.0 g) in water (50 ml) was brought to pH 5.5 with acetic acid. Tungstophosphoric acid (7 g) was added followed by a solution of trans-[(C$_2$H$_5$)$_3$P]$_2$Pt(H)SnCl$_3$ (1.5 g) in tetrahydrofuran (10 ml). The mixture was stirred for five minutes and then filtered. The addition of excess trimethylammonium chloride to the filtrate gave a precipitate containing a hydrate of [(CH$_3$)$_3$NH]$_4$[(C$_2$H$_5$)$_3$P]$_2$Pt(H)SnW$_{11}$PO$_{39}$.

| Anal. Calc'd for [(CH$_3$)$_3$NH]$_4$[(C$_2$H$_5$)$_3$P]$_2$Pt(H)SnW$_{11}$PO$_{39}$ . 4H$_2$O: | | | | | | | | | |
|---|---|---|---|---|---|---|---|---|---|
| | C, | 8.14; | H, | 2.22; | N, | 1.58; | O, | 19.43; | |
| | Sn, | 3.35; | Pt, | 5.51; | H$_2$O, | 2.03 | | | |
| Found: | C, | 8.64; | H, | 1.96; | N, | 1.24; | O, | 19.47; | |
| | | 8.62 | | 2.07 | | 1.30 | | 18.99 | |
| | | | | | | | | 19.18 | |
| | Sn, | 3.45; | Pt, | 7.36; | H$_2$O, | 2.09 | | | |
| | | 3.30 | | 7.55 | | 2.30 | | | |

The infrared absorption spectrum (mineral-oil mull) exhibited a band at about 2120 cm$^{-1}$, assignable to the Pt-H moiety

INDUSTRIAL APPLICABILITY

As shown in following Examples A, B, C, and D, the products of the invention are catalysts for the oligomerization of terephthalic acid with ethylene glycol. This oligomerization is an important step in the preparation of commercial polyester. Examples B, C and D show that the products have significantly higher catalytic activity than the commercially available heteropolyanionic compound of Example A.

EXAMPLE A (Control)

A mixture of terephthalic acid (41.5 g), ethylene glycol (31.0 g) and $Na_4W_{12}SiO_{40}$ (510.4 mg; commercial sample, probably hydrated) was heated at 240.8°–241° for six hours in such a fashion that the water formed was removed by distillation. No clear oligomer was formed; the amount of water separated indicated 42% conversion to oligomer.

EXAMPLE B

Example A was repeated, with 520 mg of $[(CH_3)_3NH]_{11}(CO)_3Co(SnW_{11}SiO_{39})_2 \cdot 3H_2O$ in place of the $Na_4W_{12}SiO_{40}$. The temperature range was 240.4°–241°. The amount of water formed indicated 91% conversion to an oligomer, which was cloudy pink in appearance.

EXAMPLE C

Example B was repeated with 520 mg of $[(CH_3)_3NH]_4C_5H_5Fe(CO)_2SnW_{11}PO_{39}$ as a catalyst with a reaction time of 4.3 hours at 240.4°–241°. A 90% conversion to a clear yellow oligomer was obtained.

EXAMPLE D

Example C was repeated with 500 mg of $K_9(CO)_3Co(SnW_{11}PO_{39})_2 \cdot 6H_2O$ as catalyst with a reaction period of 4.5 hours at a temperature of 240.8° to 241°. A clear colorless oligomer was obtained (83% conversion).

Examples E and F show that the novel heteropolyacids of the invention, which are made by cation-exchange from the salts, are catalysts for the isomerization of 1-butene, and for the dehydration of 2-butanol and the subsequent isomerization of the 1-butane thus formed.

EXAMPLE E

An aqueous solution of $[(CH_3)_3NH]_4[\pi\text{-}C_5H_5Fe(CO)_2Fe]_2W_{11}SiO_{40}$ (5 g) was passed through an ion-exchange column containing an excess of a crosslinked poly(styrenesulfonic acid) cation exchange resin. The effluent was evaporated to dryness to leave an orange, glossy residue which was a hydrate of $H_4(\pi\text{-}C_5H_5Fe(CO)_2GeOH)_2W_{11}SiO_{39}$. Part of this (43 mg) was dissolved in ethanol. Silica (10 g, 750 sq meters/g surface area) was added and the solution was evaporated to obtain the heteropolyacid supported on the silica. This product was dried one hour at 150° in vacuum. The resulting catalyst was then used as follows:

a. The catalyst (1 g) and toluene (10 ml) were stirred in a glass pressure bottle under 20–23 psig pressure of 1-butene at 60° for seven hours. Gas chromatographic/mass spectrographic analysis indicated that the readily volatile fraction contained 96.8% of 1-butene, 1.2% cis-2-butene and 1.3% trans-2-butene. Better results were obtained in a flow system:

b. The same catalyst (3.0g) was placed in a ¾" diameter tube to form a catalyst bed 1½" long. 1-Butene was passed through this bed at 60° at a flow rate of 20 ml/min. The effluent was found by gas chromatographic/mass spectrographic analysis to consist of 34% 1-butene; 31% cis-2-butene and 35% trans-2-butene.

EXAMPLE F

2-Butanol (flow rate 1 ml/10 minutes) and nitrogen (flow rate 20 ml/minute) were passed together through the catalyst recovered from Example Eb, in the same reactor, for one hour at 150°. The effluent was passed through an ambient temperature trap, which collected 1.25 g of a mixture of butanol and water, and then through a trap cooled with solid carbon dioxide. The latter trap condensed 4 ml of a liquid shown by gas chromatography to be a mixture of butenes, primarily cis and trans 2-butene.

I claim:

1. Salts and acids containing a triheteropolyanion in which one addenda atom of a heterododecatungstate or heterododecamolybdate is replaced by one tin atom or by two germanium atoms, in which the tin atom or the germanium atoms are bonded to a ligated transition metal, the central atom of the heterododecaanion is not bonded directly to the ligated transition metal-tin moiety or the ligated transition metal-germanium moiety, the added ligated transition metal is not part of the dodecanuclear cage structure, the heteropolyanion contains at least one metal-metal bond which is outside the skeletal structure of the heteropolyanion, and the salts and acids are of a formula selected from the group consisting of

   (1)

   (2)

   (3)

   (4)

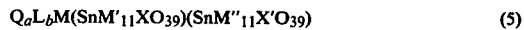   (5)

and

   (6)

in which

Q is one equivalent of a cation;

$L_bM$ is a ligated transition metal M bonded to b ligands L, b is at least 1, and the ligands are the same or different when b is greater than 1;

M' and M" are W or Mo;

X and X' are Si, P, Co or Ge; with the proviso that at least one of M" and X' is different from M' and X, respectively;

a is the number of formal negative charges on the heteropolyanion; and y is the degree of polymerization.

2. The salts and acids of claim 1 of the formula $Q_aL_bMSnM'_{11}XO_{39}$.

3. The salts and acids of claim 1 of the formula $Q_aL_{b-1}M(SnM'_{11}XO_{39})_2$.

4. The salts and acids of claim 3 of the formula $Q_a\pi\text{-}C_3H_5Pd(SnM'_{11}XO_{39})_2$.

5. The salts and acids of claim 4 of the formula $Q_a\pi\text{-}C_3H_5Pd(SnW_{11}XO_{39})_2$.

6. The salts and acids of claim 5 of the formula $Q_a\pi\text{-}C_3H_5Pd(SnW_{11}SiO_{39})_2$.

7. The salts and acids of claim 1 of the formula $Q_a(L_bMGe)_2M'_{11}XO_{40}$.

* * * * *